(12) United States Patent
Gostjeva et al.

(10) Patent No.: US 9,499,851 B2
(45) Date of Patent: Nov. 22, 2016

(54) WOUND HEALING METAKARYOTIC STEM CELLS AND METHODS OF USE THEREOF

(75) Inventors: Elena V. Gostjeva, Winchester, MA (US); William G. Thilly, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/879,675

(22) PCT Filed: Oct. 24, 2011

(86) PCT No.: PCT/US2011/057513
§ 371 (c)(1),
(2), (4) Date: Apr. 16, 2013

(87) PCT Pub. No.: WO2012/061073
PCT Pub. Date: May 10, 2012

(65) Prior Publication Data
US 2013/0203048 A1  Aug. 8, 2013

Related U.S. Application Data

(60) Provisional application No. 61/406,468, filed on Oct. 25, 2010.

(51) Int. Cl.
*C12Q 1/02* (2006.01)
*G01N 33/50* (2006.01)
*G01N 33/68* (2006.01)

(52) U.S. Cl.
CPC ........... *C12Q 1/025* (2013.01); *G01N 33/5058* (2013.01); *G01N 33/6893* (2013.01)

(58) Field of Classification Search
CPC ............ G01N 33/5073; G01N 33/5044; G01N 33/5058; G01N 33/6893; C12Q 1/025
See application file for complete search history.

(56) References Cited

U.S. PATENT DOCUMENTS

| | | |
|---|---|---|
| 5,369,002 A | 11/1994 | Fukuda |
| 6,007,996 A | 12/1999 | McNamara et al. |
| 7,427,502 B2 | 9/2008 | Gostjeva et al. |
| 7,850,961 B2 | 12/2010 | Clarke et al. |
| 7,977,092 B2 | 7/2011 | Gostjeva et al. |
| 8,465,943 B2 | 6/2013 | Gostjeva et al. |
| 8,940,500 B2 | 1/2015 | Gostjeva et al. |
| 2006/0083682 A1 | 4/2006 | Bergstein |
| 2006/0134668 A1 | 6/2006 | Markowitz |
| 2009/0081720 A1 | 3/2009 | Gostjeva et al. |
| 2009/0098562 A1* | 4/2009 | Gostjeva et al. ........... 435/6 |
| 2009/0304662 A1 | 12/2009 | Thilly et al. |
| 2010/0075366 A1* | 3/2010 | Gostjeva et al. ........... 435/29 |
| 2010/0284905 A1 | 11/2010 | Gostjeva et al. |
| 2014/0154672 A1 | 6/2014 | Gostjeva et al. |
| 2014/0369934 A1 | 12/2014 | Thilly et al. |

FOREIGN PATENT DOCUMENTS

| | | |
|---|---|---|
| EP | 2171448 B | 8/2012 |
| IL | 179972 | 12/2011 |
| JP | Sho-62-008053 | 1/1987 |
| JP | 2008-283989 A | 11/2008 |
| JP | 2009-280820 A | 12/2009 |
| JP | 5130042 | 11/2012 |
| JP | 5171945 | 1/2013 |
| KR | 10-1209833 | 12/2012 |
| WO | WO 2005/097147 A1 | 10/2005 |
| WO | WO 2006/009860 A2 | 1/2006 |
| WO | WO 2007/067795 | 6/2007 |
| WO | WO 2008/115517 | 9/2008 |
| WO | WO 2008/156629 | 12/2008 |
| WO | WO 2010/036322 A1 | 4/2010 |
| WO | WO 2012/061073 A1 | 5/2012 |

OTHER PUBLICATIONS

Rittershaus et al. (Arch Pathol Lab Med. 2011; 135: 1311-1319).*
Richard Phipps (PNAS, Jun. 20, 2000; 97(13): 6930-6932).*
Kanzaki, M., et al., "Bilateral Endobronchial Metastasis in Postoperataive Stage I Pulmonary Adenocarcinoma," *Diagnostic and Therapeutic Endoscopy*, 6: 141-145 (2000).
Thilly, W. G., et al., "Metakaryotic stem cell nuclei use pangenomic dsRNA/DNA intermediates in genome replication and segregation," *Organogenesis*, 10(1): 1-9 (2014).
Office Action from Canadian Application No. 2,570,422, "Methods for Identifying Stem Cells Based on Nuclear Morphotypes," mailed Mar. 7, 2013.
Office Action from Chinese Application No. 2009801461148.2, "Methods for Identifying Stem Cells by Detecting Fluorescence of Cells and Syncytia," mailed Apr. 17, 2013.
Office Action from European Application No. 09 736 317.0, "Methods for Identifying Stem Cells by Detecting Fluorescence of Cells and Syncytia," mailed Aug. 28, 2013.
Reply from Canadian Application No. 2,570,422, "Methods for Identifying Stem Cells Based on Nuclear Morphotypes," filed Sep. 9, 2013.
Office Action from Chinese Application No. 200880020171.3, "Method and Agents for Inhibiting Tumor Growth by Targeting the ssDNA Replication Intermediate of Tumor Stem Cells," mailed on Oct. 6, 2013.
Reexamination Decision from Chinese Application No. 200580027499.4, "Methods for Identifying Stem Cells Based on Nuclear Morphotypes," mailed Nov. 4, 2013.
Office Action from Chinese Application No. 2009801461148.2, "Methods for Identifying Stem Cells by Detecting Fluorescence of Cells and Syncytia," mailed Nov. 22, 2013.
International Preliminary Report on Patentability from International Application No. PCT/US2012/040361, "dsRNA/DNA Hybrid Genome Replication Intermediate of Metakaryotic Stem Cells," mailed Dec. 12, 2013.

(Continued)

*Primary Examiner* — Scott Long
(74) *Attorney, Agent, or Firm* — HoustonHogle LLP

(57) ABSTRACT

The invention provides methods of identifying wound healing metakaryotic stem cells, identifying molecules to modulate proliferation and/or migration of metakaryotic stem cells and molecules to treat wound healing disorders, such as blood vessel wound healing disorders, including restenosis. The invention also provides methods of diagnosing and treating wound healing disorders, such as blood vessel wound healing disorders and also of treating wounds by the use of metakaryotic stem cell transplant(s).

17 Claims, 33 Drawing Sheets

(56) References Cited

OTHER PUBLICATIONS

Reply from European Application No. 09 736 317.0, "Methods for Identifying Stem Cells by Detecting Fluorescence of Cells and Syncytia," filed Dec. 20, 2013.
Office Action from Chinese Application No. 200580027499.4, "Methods for Identifying Stem Cells Based on Nuclear Morphotypes," mailed Dec. 23, 2013.
Office Action from Indian Application No. 2561/CHENP/2011, "Methods for Identifying Stem Cells by Detecting Fluorescence of Cells and Syncytia," mailed Dec. 30, 2013.
Office Action from Japanese Application No. 2011-527826, "Methods for Identifying Stem Cells by Detecting Fluorescence of Cells and Syncytia," mailed Feb. 17, 2014.
Restriction Requirement from U.S. Appl. No. 13/914,152, mailed Mar. 11, 2014.
Abe, T., et al., "Myocyte Differentiation Generates Nuclear Invaginations Traversed by Myofibrils Associating with Sarcomeric Protein mRNAs," *Journal of Cell Science*, 117: 6523-6534 (2004).
Al-Hajj, M., and Clarke, M. F., "Self-Renewal and Solid Tumor Stem Cells," *Oncogene*, 23: 7274-7282 (2004).
Andersson, G. K. A., et al., "Exposure and Removal of Stainable Groups During Feulgen Acid Hydrolysis of Fixed Chromatin at Different Temperatures," *Histochemie*, 27: 165-172 (1971).
Biesterfeld, S., et al., "DNA Image Cytometry in the Differential Diagnosis of Endometrial Hyperplasia and Adenocarcinoma," *Analyt. Quant. Cytol. Histol.*, 23: 123-128 (2001).
Boman, B. M., et al., "Cancer Stem Cells: A Step Toward the Cure," *J. Clinical Oncology*, 26(17): 2795-2799 (2008).
Cairns, J., "Mutation Selection and the Natural History of Cancer," *Nature*, 255: 197-200 (1975).
Chari, R. S., et al., "Preoperative Radiation and Chemotherapy in the Treatment of Adenocarcinoma of the Rectum," *Annals of Surgery*, 221: 778-787 (1995).
Chen, W., et al., "High Frequency of NPM1 Gene Mutations in Acute Myeloid Leukemia with Prominent Nuclear Invaginations ("cuplike" nuclei)," *Blood*, 108(5): 1783:1784 (2006).
Clark, A. D., et al., "Isolation and therapeutic potential of human haemopoietic stem cells," *Cytotechnology*, 41(2-3): 111-31 (2003) (Abstract only).
Cutts, S. M., et al., "Defective Chromosome Segregation, Microtubule Bundling and Nuclear Bridging in Inner Centromere Protein Gene (Incep)-Disrupted Mice," *Human Molecular Genetics*, 8(7): 1145-1155 (1999).
Drezek, R., et al., "Light Scattering from Cervical Cells Throughout Neoplastic Progression: Influence of Nuclear Morphology, DNA Content, and Chromatin Texture," *J. Biomed. Optics*, 8: 7-16 (2003).
Fischer, P. M., "Recent Progress in the Discovery and Development of Cyclin-Dependent Kinase Inhibitors," *Expert Opinion on Investigational Drugs*, 14(4) (2005) (Abstract only).
Folkman, J., and Ingber, D., "Inhibition of Angiogenesis," *Cancer Biology*, 3: 88-96 (1992).
Fujiu, K., and Numata, O., "Reorganization of Microtubules in the Amitotically Dividing Macromolecules of Tetrahymena," *Cell Motility and Cytoskeleton*, 46: 17-27 (2000).
Gibson, P. R., et al., "Isolation of Colonic Crypts That Maintain Structural and Metabolic Viability in Vitro," *Gastroenterology*, 96: 283-291 (1989).
Gómez-Vidal, J. A., et al, "Actual Targets in Cytodifferentiation Cancer Therapy," *Current Topics in Medicinal Chemistry*, 4: 175-202 (2004).
Gosteva, E. V., "Densitometric Scanning of Plant Chromosomes Aimed at Their Identification," *Cytology and Genetics*, 32(5): 13-16 (1998).
Gostjeva, E. V., et al., "Bell-Shaped Nuclei Dividing by Symmetrical and Asymmetrical Nuclear Fission Have Qualities of Stem Cells in Human Colonic Embryogenesis and Carcinogenesis," *Cancer Gen. and Cytogenetics*, 164: 16-24 (2006).
Gostjeva, E. V., et al., "Metakaryotic stem cell lineages in organogenesis of humans and other metazoans," *Organogenesis*, 5(4): 191-200 (2009).
Gostjeva, E. V., et al., "Nuclear Morphotypes in Human Embryogenesis and Carcinogenesis: Bell-Shaped Nuclei Show Stem-Like Properties in Vivo," *Environmental and Molecular Mutagenesis*, 47(6): 405 (2006).
Gostjeva, E. V., and Thilly, W. G., "Stem Cell Stages and the Origins of Colon Cancer," *Stem Cell Reviews*, 1: 243-252 (2005).
Gruhl, A. N., et al., "Human fetal/tumor metakaryotic stem cells: pangenomic homologous pairing and telomeric end-joining of chromatids," *Cancer Genetics and Cytogenetics*, 203(2): 203-208 (2010).
Hardie, D. C., el al., "From Pixels to Picograms: A Beginners' Guide to Genome Quantification by Feulgen Image Analysis Densitometry," *J. Histochemistry & Cytochemistry*, 50(6): 735-749 (2002).
Herrero-Jimenez, P., et al., "Mutation, Cell Kinetics, and Subpopulations at Risk for Colon Cancer in the United States," *Mutat. Res.*, 400: 553-578 (1998).
Herrero-Jimenez, P., et al., "Population Risk and Physiological Rate Parameters for Colon Cancer: The Union of an Explicit Model for Carcinogenesis with the Public Health Records of the United States," *Mutat. Res.*, 447: 73-116 (2000).
Hirokawa, M., et al., "Gastrointestinal Stromal Tumor with Skeinoid Fibers of the Ileum," *Diagnostic Cytopathology*, 23(4): 266-268 (2000).
Itoi, T., et al., "Detection of Telemerase Activity in Biopsy Specimens for Diagnosis of Biliary Tract Cancers," *Gastrointestinal Endoscopy*, 52: 380-386 (2000).
James, H. A., "The Potential Application of Ribozymes for the Treatment of Hematological Disorders," *J. Leukocyte Biology*, 66: 361-368 (1999).
Kjellstrand, P., "Mechansim of the Feulgen Acid Hydrolysis," *J. Microscopy*, 119(3): 391-396 (1980).
Klijanienko, J., et al., "Fine-Needle Aspiration of Leiomyosarcoma: A Correlative Cytohistopathological Study of 96 Tumors in 68 Patients," *Diagn. Cytopathol.*, 28: 119-125 (2003).
Kussick, S. J., et al., "A Distinctive Nuclear Morphology in Acute Myeloid Leukemia is Strongly Associated with Loss of HLA-DR Expression and FLT Internal Tandem Duplication," *Leukemia*, 18: 1591-1598 (2004).
Liu, K., et al., "Logistic Regression Analysis of High Grade Spindle Cell Neoplasms," *ACTA Cytologica*, 43(4): 593-600 (1999).
Lodding, P., et al., "Cellular Schwannoma," *Virchows Archiv.*, 416: 237-248 (1990).
Lo Muzio, L., et al., "Primary intraoral leiomyosarcoma of the tongue: an immunohistochemical study and review of the literature," *Oral Oncology*, 36(6): 519-524 (2000).
Maly, B., et al., "Fine Needle Aspiration Biopsy of Intraparotid Schwannoma: A case report," *ACTA Cytologica*, 47(6): 1131-1134 (2003).
Merok, J. R., et al., "Cosegregation of Chromosomes Containing Immortal DNA Strands in Cells that Cycle with Asymmetric Stem Cell Kinetics," *Cancer Res.*, 62: 6791-5 (2002).
Munoz, L., et al., "Actue myeloid leukemia with MLL rearrangements: clinicobiological features, prognostic impact and value of flow cytometry in the detection of residual leukemic cells," *Leukemia*, 17: 76-82 (2003).
Otto, W. R., "Lung Epithelial Stem Cells," *J. Pathology*, 197: 527-535 (2002).
Özkinay, C., and Mitelman, F., "A Simple Trypsin-Giemsa Technique Producing Simultaneous G- and C-Banding in Human Chromosomes," *Hereditas*, 90: 1-4 (1979).
Potten, C. S., et al., "Intestinal Stem Cells Protect Their Genome by Selective Segregation of Template DNA Strands," *J. Cell Science*, 115: 2381-2388 (2002).
Refinetti, P., "Analysis of familial risk for prostate, colon and female breast cancer in Sweden," Master's project in Bioengineering and Biotechnology [online] [retrieved onJul. 26, 2012]. Retrieved from the Internet URL: infoscience.eptl.ch/record/173435/files/Master_thesis_Final.pdf.

(56) References Cited

OTHER PUBLICATIONS

Ruddy, J. M. B., and Majumdar, S. K., "Antitumorigenic Evaluation of Thalidomide Alone and in Combination with Cisplatin in DBA2/J Mice," *J. Biomedicine and Biotechnology*, 2: 7-13 (2002).
Sakaki, M., et al., "Gallbladder Adenocarcinoma with Florid Neuroendocrine Cell Nests and Extensive Paneth Cell Metaplasia," *Endocrine Pathology*, 11(4): 365-371 (2000).
Scheidl, S. J., et al., "mRNA Expression Profiling of Laser Microbeam Microdissected Cells from Slender Embryonic Structures," *Am. Jour. Path.*, 160: 801-813 (2002).
Sell, S., "Stem Cell Origin of Cancer and Differentiation Therapy," *Critical Reviews in Oncology/Hematology*, 51: 1-28 (2004).
Silverman, J. S., and Brustein, S., "Myxoid Dermatofibrohistiocytoma: An Indolent Post-Traumatic Tumor Composed of CD34+ Epitheliod and Dendtritic Cells and Factor XIIIa+ Dendrophages," *J. Cutan. Pathol.*, 23: 551-557 (1996).
Sperr, W. R., et al., "Human Leukaemic Stem Cells: A Novel Target of Therapy," *European J. Clinical Investigation*, 34(Suppl. 2): 31-40 (2004).
Thilly, W. G., "Metakaryotic Biology, a Revolution in Cancer Stem Cell Research" [online] [retrieved onJul. 26, 2012]. Retrieved from the Internet URL: www.med.uio.no/klinmet/english/research/news-and-events/events/guest-lectures-seminars/2012/william-thilly.html.
Venezia, T. A., et al., "Molecular Signatures of Proliferation and Quiescence in Hematopoietic Stem Cells," *PLoS Biology*, 2(10): 1640-1651 (2004).
Wadkins, R. M., et al., "Actinomycin D Binds to Metastable Hairpins in Single-Stranded DNA," *Biochemistry*, 37(34): 11915-11923 (1998).
White, R. J., et al., "Development of Mitoxantrone," *Investigational New Drugs*, 3(2): 85-93 (1985).
Ying, Z., et al., "Expression of Neural Stem Cell Surface Marker CD133 in Balloon Cells of Human Focal Cortical Dysplasia," *Epilepsia*, 46(11): 1716-1723 (2005).
Invitation to Pay Additional Fees with Partial International Search Report from International Application No. PCT/US2005/021504, "Methods for Identifying Stem Cells Based on Nuclear Morphotypes," mailed Mar. 24, 2006.
International Search Report and Written Opinion from International Application No. PCT/US2005/021504, "Methods for Identifying Stem Cells Based on Nuclear Morphotypes," mailed May 5, 2006.
International Preliminary Report on Patentability from International Application No. PCT/US2005/021504, "Methods for Identifying Stem Cells Based on Nuclear Morphotypes," mailed Jan. 4, 2007.
International Search Report and Written Opinion from International Application No. PCT/US2006/047136, "Methods for Identifying and Targeting Tumor Stem Cells Based on Nuclear Morphology," mailed Jun. 27, 2007.
International Preliminary Report on Patentability from International Application No. PCT/US2006/047136, "Methods for Identifying and Targeting Tumor Stem Cells Based on Nuclear Morphology," mailed Jun. 19, 2008.
Invitation to Pay Additional Fees with Partial International Search Report from International Application No. PCT/US2008/003604, "Methods for Identifying Stem Cells by Detecting Autofluorescence of Cells and Syncytia," mailed Aug. 12, 2008.
International Search Report and Written Opinion from International Application No. PCT/US2008/003604, "Methods for Identifying Stem Cells by Detecting Autofluorescence of Cells and Syncytia," mailed Jan. 19, 2009.
International Preliminary Report on Patentability from International Application No. PCT/US2008/003604, "Methods for Identifying Stem Cells by Detecting Autofluorescence of Cells and Syncytia," mailed Oct. 1, 2009.
International Search Report and Written Opinion from International Application No. PCT/US2008/007327, "Methods and Agents for Inhibiting Tumor Growth," mailed Dec. 2, 2008.
International Preliminary Report on Patentability from International Application No. PCT/US2008/007327, "Methods and Agents for Inhibiting Tumor Growth," mailed Dec. 30, 2009.
Office Action from Israeli Application No. 179972, dated Sep. 7, 2009.
International Search Report and Written Opinion from International Application No. PCT/US2009/005241, "Methods for Identifying Stem Cells by Detecting Fluorescence of Cells and Syncytia," mailed Jan. 2, 2010.
Reply from Israeli Application No. 179972, filed Mar. 3, 2010.
Office Action from European Application No. 05761437.2, dated Mar. 26, 2010.
Office Action from Indian Application No. 3481/CHENP/2008, received Mar. 31, 2010.
Office Action from Australian Application No. 2006321710, dated Jun. 11, 2010.
Office Action from Israeli Application No. 179972, dated Jul. 6, 2010.
Office Action from Israeli Application No. 191746, dated Jul. 14, 2010.
Office Action from European Application No. 08768379.3, dated Aug. 2, 2010.
Restriction Requirement from U.S. Appl. No. 12/085,533, dated Sep. 1, 2010.
Office Action from Chinese Application No. 200680052588.9, dated Sep. 14, 2010.
Reply from European Application No. 05761437.2, filed Oct. 5, 2010.
Office Action from Chinese Application No. 200580027499.4, dated Oct. 21, 2010.
Office Action from Japanese Application No. 2007-516787, dated Dec. 14, 2010.
Restriction Requirement from U.S. Appl. No. 12/283,727, dated Jan. 27, 2011.
Reply to Restriction Requirement from U.S. Appl. No. 12/085,533, filed Jan. 31, 2011.
Reply from European Application No. 08768379.3, filed Feb. 11, 2011.
Restriction Requirement from U.S. Appl. No. 12/284,521, dated Feb. 17, 2011.
Reply to Restriction Requirement from U.S. Appl. No. 12/283,727, filed Mar. 1, 2011.
Office Action from U.S. Appl. No. 12/085,533, dated Mar. 18, 2011.
Reply to Restriction Requirement from U.S. Appl. No. 12/284,521, filed Mar. 21, 2011.
International Preliminary Report on Patentability from International Application No. PCT/US2009/005241, "Methods for Identifying Stem Cells by Detecting Fluorescence of Cells and Syncytia," mailed Apr. 7, 2011.
Office Action from U.S. Appl. No. 12/283,727, dated Apr. 7, 2011.
Notice of Allowance from U.S. Appl. No. 12/284,521, dated May 9, 2011.
Summons to Attend Oral Proceedings from European Application No. 08768379.3, dated May 12, 2011.
Communication Pursuant to Rules 161(1) and 162 EPC from European Application No. 09736317.0, dated May 30, 2011.
Reply from U.S. Appl. No. 12/283,727, filed Aug. 5, 2011.
Office Action from Japanese Application No. 2007-516787, dated Aug. 22, 2011.
Final Office Action from U.S. Appl. No. 12/283,727, dated Sep. 8, 2011.
Restriction Requirement from U.S. Appl. No. 12/598,452, dated Oct. 13, 2011.
Reply to Summons from European Application No. 08768379.3, filed Dec. 12, 2011.
Reply to Restriction Requirement from U.S. Appl. No. 12/598,452, dated Dec. 13, 2011.
Restriction Requirement from U.S. Appl. No. 12/586,372, dated Jan. 11, 2012.
Reply to Restriction Requirement from U.S. Appl. No. 12/586,372, filed Feb. 13, 2012.
Notice of Grant from European Application No. 08768379.3, dated Feb. 22, 2012.

(56) References Cited

OTHER PUBLICATIONS

Office Action from Canadian Application No. 2,570,422, dated Feb. 23, 2012.
International Search Report and Written Opinion from International Application No. PCT/US2011/057513, "Wound Healing Metakaryotic Stem Cells and Methods of Use Thereof," mailed Feb. 28, 2012.
Office Action from European Application No. 05761437.2, dated Feb. 28, 2012.
Office Action from U.S. Appl. No. 12/598,452, dated Mar. 1, 2012.
Office Action from Korean Application No. 10-2007-7001187, dated Mar. 21, 2012.
Office Action from Chinese Application No. 200580027499.4, dated Mar. 27, 2012.
Office Action from U.S. Appl. No. 12/586,372 dated Apr. 11, 2012.
Office Action from Chinese Application No. 200880020171.3, dated Apr. 24, 2012.
Office Action from Japanese Application No. 2010-512184, dated May 28, 2012.
Reply from U.S. Appl. No. 12/598,452, filed Jun. 1, 2012.
Office Action from Japanese Application No. 2007-516787, dated Jun. 4, 2012.
Final Office Action from U.S. Appl. No. 12/598,452, dated Aug. 7, 2012.
Reply from U.S. Appl. No. 12/586,372, filed Aug. 13, 2012.
Reply from Canadian Application No. 2,570,422, filed Aug. 22, 2012.
Reply from European Application No. 05761437.2, filed Sep. 4, 2012.
Office Action from Chinese Application No. 200580027499.4, dated Sep. 19, 2012.
International Search Report and Written Opinion from International Application No. PCT/US2012/040361, "dsRNA/DNA Hybrid Genome Replication Intermediate of Metakaryotic Stem Cells," mailed Oct. 1, 2012.
Final Office Action from U.S. Appl. No. 12/586,372, dated Oct. 3, 2012.
Reply and Request for Continued Examination from U.S. Appl. No. 12/283,727, filed Oct. 5, 2012.
Final Office Action from U.S. Appl. No. 12/283,727, dated Nov. 2, 2012.
Request for Continued Examination from U.S. Appl. No. 12/598,452, filed Jan. 10, 2013.
Reply from U.S. Appl. No. 12/586,372, filed Feb. 1, 2013.
Request for Continued Examination from U.S. Appl. No. 12/586,372, filed Feb. 27, 2013.
Office Action from Chinese Application No. 200880020171.3, dated Mar. 1, 2013.
Reply from U.S. Appl. No. 12/283,727, filed Mar. 4, 2013.
Notice of Allowance from U.S. Appl. No. 12/283,727, dated Mar. 8, 2013.
International Preliminary Report on Patentability from International Application No. PCT/US2011/057513, "Wound Healing Metakaryotic Stem Cells and Methods of Use Thereof," mailed May 10, 2013.
Decision on Rejection, Chinese appl. 200580027499.4, dated Apr. 28, 2013.
Goodlad, R. A., et al., "Morphometry and Cell Proliferation in Endoscopic Biopsies: Evaluation of a Technique," *Gastroenterology*, 101: 1235-1241 (1991).
Jarnicki, A. G., et al., "Suppression of Antitumor Immunity by IL-10 and TGF-β-Producing T Cells Infiltrating the Growing Tumor: Influence of Tumor Environment on the Induction of CD4$^+$ and CD8$^+$ Regulatory T Cells," *J. Immunol.*, 177: 896-904 (2006).
Mocellin, S, et al., "Interleukin-10 and the immune response against cancer: a counterpoint," *J. Leukoc. Biol.*, 78: 1043-1051 (2005).
Wong, W.-M., et al., "Histogenesis of human colorectal adenomas and hyperplastic polyps: the role of cell proliferation and crypt fission," *Gut*, 50: 212-217 (2002).

Office Action from European Application No. 05 761 437.2, "Methods for Identifying Stem Cells Based on Nuclear Morphotypes," mailed Feb. 26, 2014.
Office Action from Chinese Application No. 200980146118.2, "Methods for Identifying Stem Cells by Detecting Fluorescence of Cells and Syncytia," mailed Apr. 23, 2014.
Office Action from U.S. Appl. No. 12/586,372, mailed May 1, 2014.
Office Action from Canadian Application No. 2,570,422, "Methods for Identifying Stem Cells Based on Nuclear Morphotypes," mailed May 7, 2014.
Office Action from European Application No. 09 736 317.0, "Methods for Identifying Stem Cells by Detecting Fluorescence of Cells and Syncytia," mailed May 7, 2014.
Reply from European Application No. 09 736 317.0, "Methods for Identifying Stem Cells by Detecting Fluorescence of Cells and Syncytia," filed Jun. 3, 2014.
Office Action from European Application No. 09 736 317.0, "Methods for Identifying Stem Cells by Detecting Fluorescence of Cells and Syncytia," mailed Jun. 24, 2014.
Notice of Allowance from Chinese Application No. 200580027499.4, "Methods for Identifying Stem Cells Based on Nuclear Morphotypes," mailed Jul. 4, 2014.
Reply from European Application No. 12 727 007.2, "dsRNA/DNA Hybrid Genome Replication Intermediate of Metakaryotic Stem Cells," mailed Jul. 28, 2014.
Office Action from U.S. Appl. No. 12/598,452, mailed Aug. 14, 2014.
Reply from European Application No. 09 736 317.0, "Methods for Identifying Stem Cells by Detecting Fluorescence of Cells and Syncytia," filed Aug. 18, 2014.
Office Action from Chinese Application No. 201180062704.6, "Wound Healing Metakaryotic Stem Cells and Methods of Use Thereof," mailed Aug. 27, 2014.
Office Action from U.S. Appl. No. 13/914,152, mailed Sep. 19, 2014.
Bobryshev et al., "Vascular stem/progenitor cells: current status of the problem," Cell Tissue Res (2015): 362: 1-7, Jul. 14, 2015. 7 pages.
Office Action for Canadian Application No. 2,570,422, mailed Aug. 14, 2015. 5 pages.
Office Action for Chinese Application No. 2011800627046, issued May 26, 2015, with English translation. 9 pages.
Office Action for European Application No. 11779920.5, mailed Jul. 16, 2015. 4 pages.
Office Action for European Application No. 12727007.2, mailed Jul. 23, 2015. 3 pages.
Office Action for Japanese Patent Application No. 2013-535142, mailed Jul. 15, 2015, with English translation. 5 pages.
Office Action for Korean Application No. 10-2011-7009372, mailed Oct. 15, 2015, with English translation. 8 pages.
Zybina et al., "Quantitative investigation of reproduction of gonosomal condensed chromatin during trophoblast cell polyploidization and endoreduplication in the eat-european field vole Microtus rossiaemeridionalis," Reproductive Biology and Endocrinology 2003: 1:32, Apr. 8, 2003. 12 pages.
Notice of Allowance, U.S. Appl. No. 12/586,372, dated Nov. 7, 2014.
Office Action from U.S. Appl. No. 12/598,452, mailed May 18, 2015.
Frankfurt, O.S.,"Detection of DNA damage in individual cells by flow cytometric analysis using anti-DNA monoclonal Antibody," *Exp Cell Res.* 170(2):369-380 (1987).
Office Action from EP 05761437.2, "Methods for Identifying Stem Cells Based on Nuclear Morphotypes," dated Oct. 16, 2014.
Office Action from EP 12727007.2, "dsRNA/DNA Hybrid Genome Replication Intermediate of Metakaryotic Stem Cells," dated Dec. 10, 2014.
Office Action from CN 201280038235.9, dated Feb. 3, 2015.
Allowance Email received Nov. 30, 2015, from China Patent Application No. 201180062704.6, filed on Oct. 24, 2011. Two pages.
Office Action mailed on Dec. 3, 2015, from Canada Application No. 2,692,072, filed on Jun. 12, 2008. Five pages.

(56) References Cited

OTHER PUBLICATIONS

Office Action mailed Jan. 29, 2016 from European Application No. 11779920.5 filed on Oct. 24, 2011. Four pages.
Office Action dated Feb. 9, 2016, from Japanese Patent Application No. 2014-513725, filed on Jun. 1, 2012. Six pages.
Pohjoismaki, J.L.O., "Mammalian mitochondrial DNA replication intermediates are essentially duplex, but contain extensive tracts of RNA/DNA hybrid," J Mol Biol, 397(5): 1144-1155 (2010). Twenty pages.
Re-Examination Decision dated Dec. 29, 2015 attached to Chinese Associate's Letter, from China Application No. 200880020171.3, filed on Jun. 12, 2008. Eight pages.
Decision of Rejection Notice, dated Apr. 20, 2016, with Letter from Associate, from Japan Application No. 2013-535142, filed on Oct. 24, 2011. Two pages.
Office Action dated Apr. 26, 2016 from Canadian Application No. 2,738,133, filed Sep. 21, 2009. Five pages.
Notice of Allowance dated Jun. 10, 2016, from European Application No. 12727007.2, filed on Jun. 1, 2012. Five pages.
Yang,. M.Y. et al., "Biased Incorporation of Ribonucleotides on the Mitochondrial L-Strand Accounts for Apparent Strand-Asymmetric DNA Replication," Cell, 111:495-505 (2002).

\* cited by examiner

Fig. 2
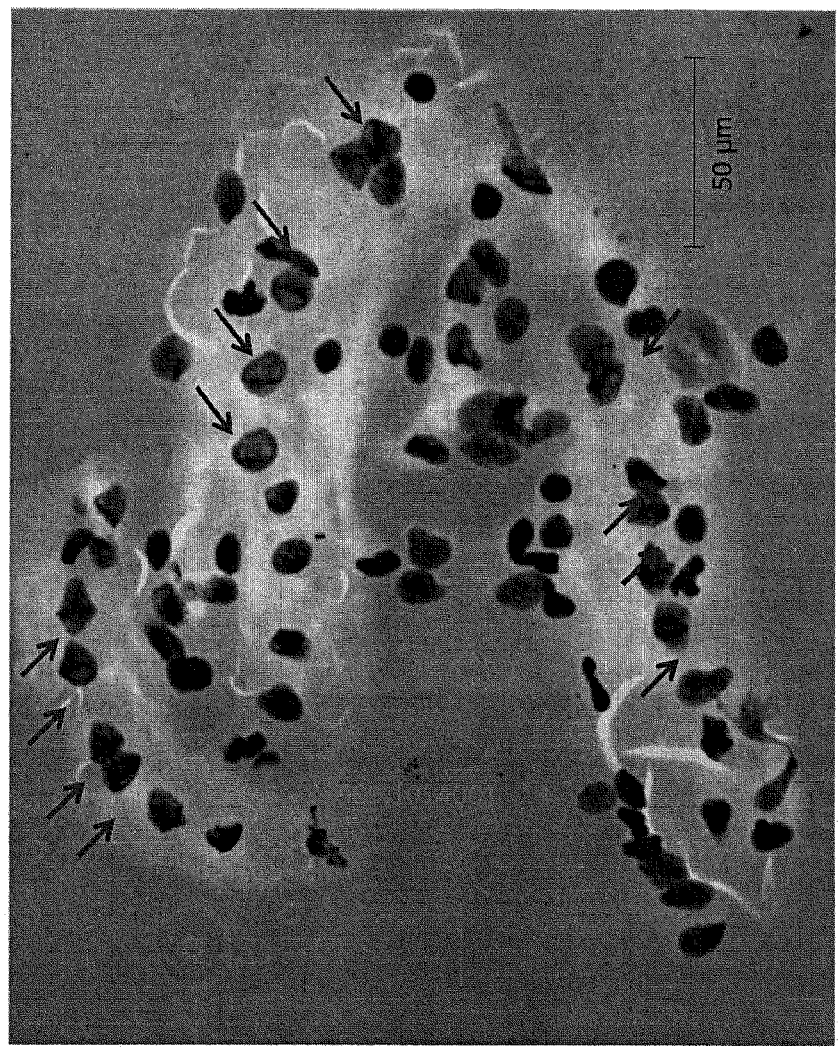
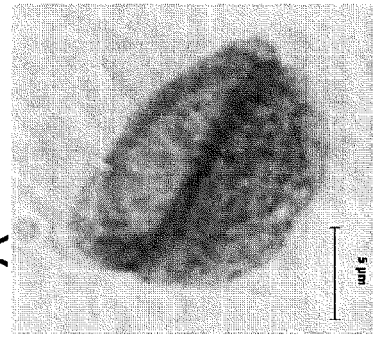

FIG. 7
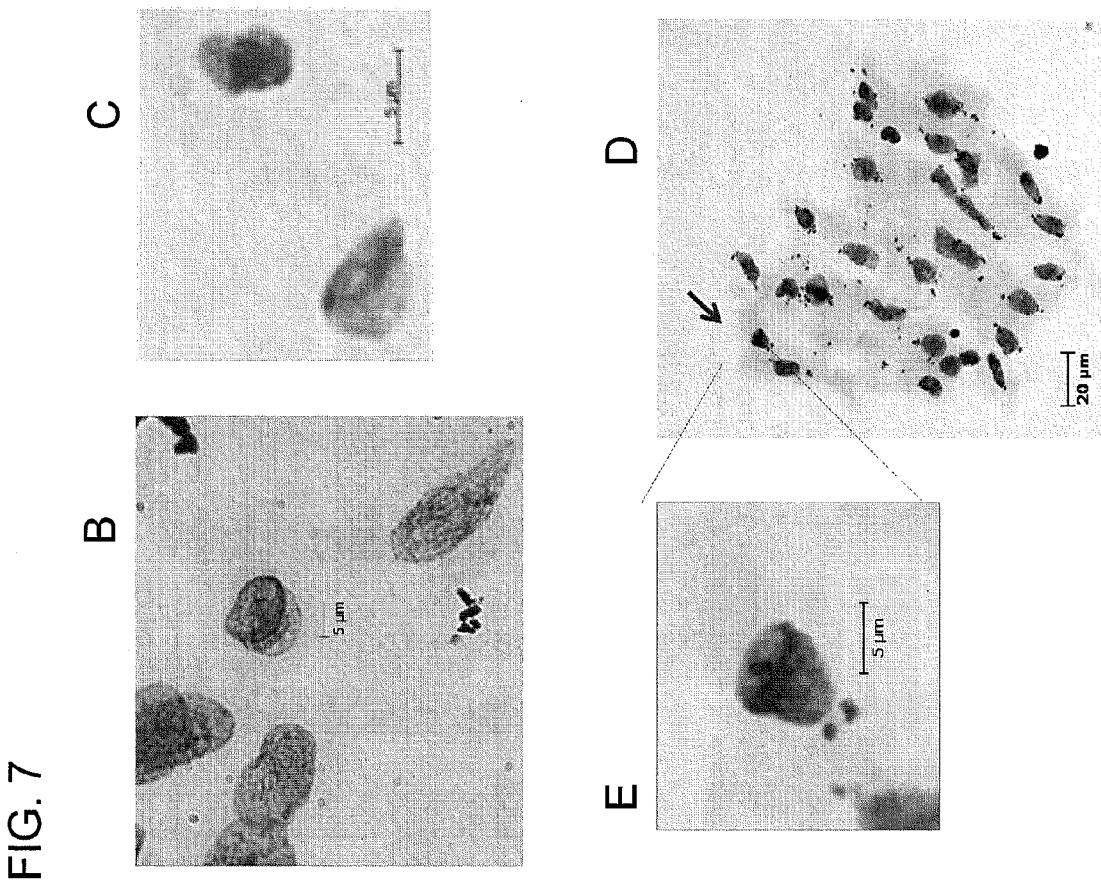
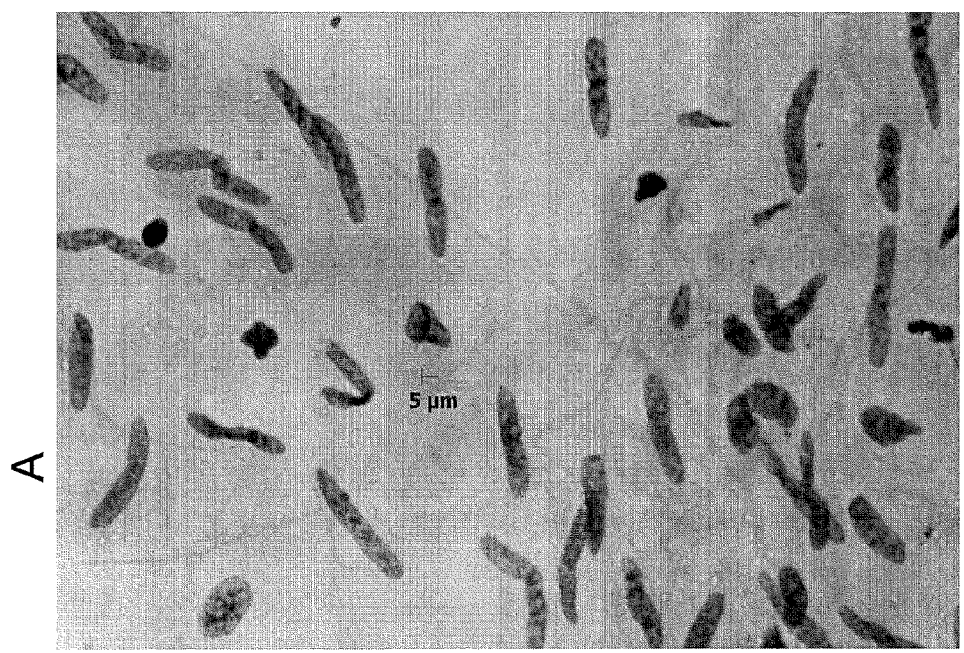

FIG. 9
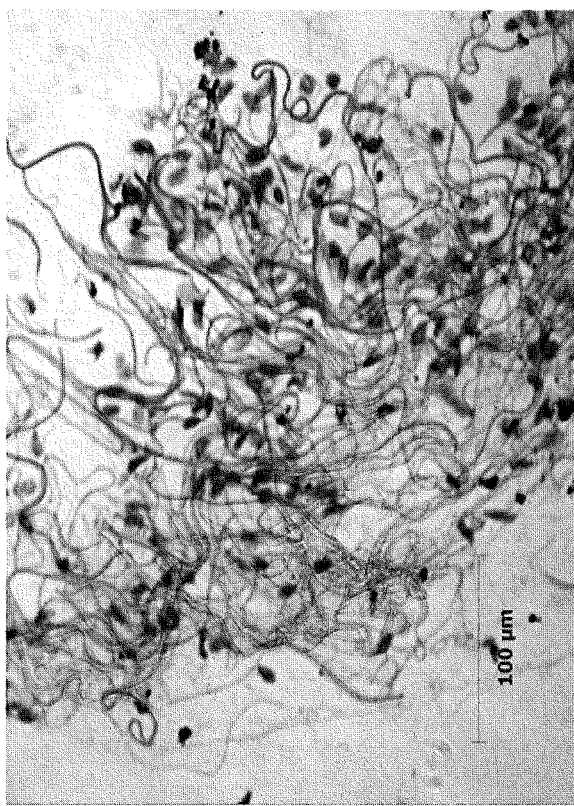

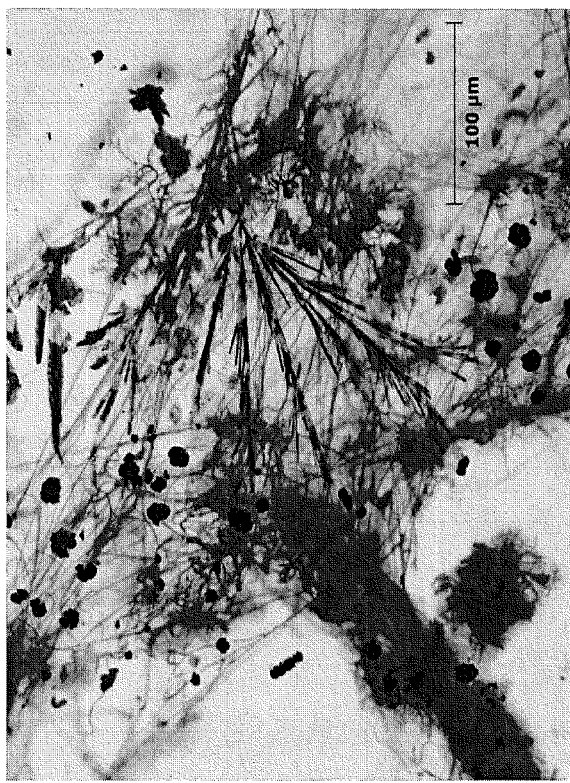 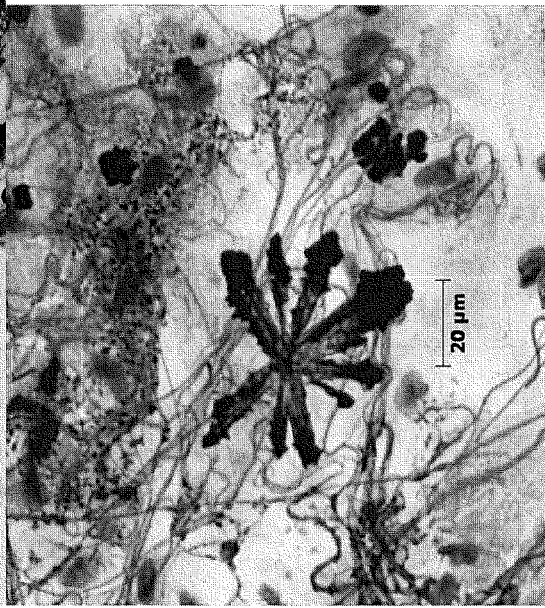
FIG. 10

FIG. 15
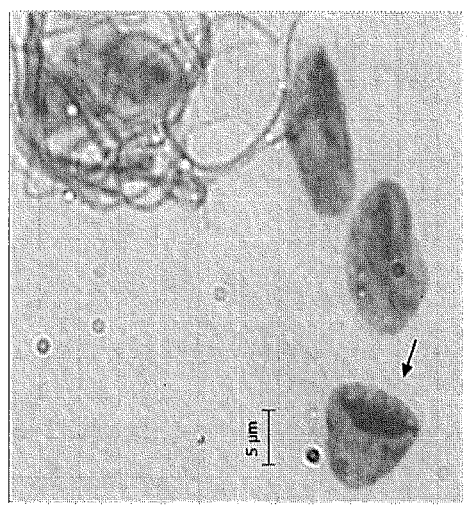
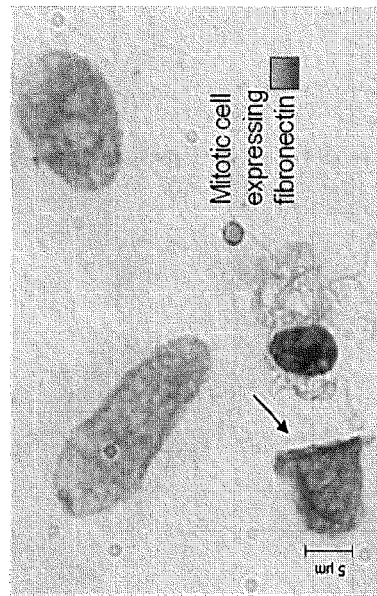
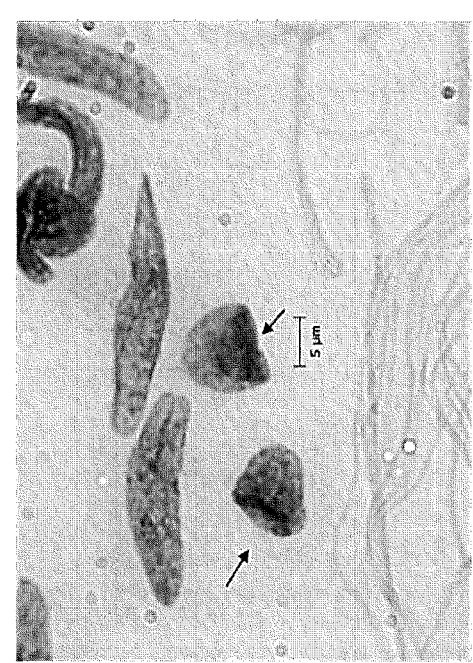

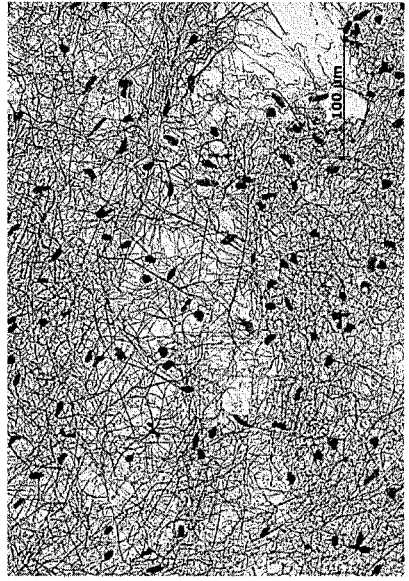
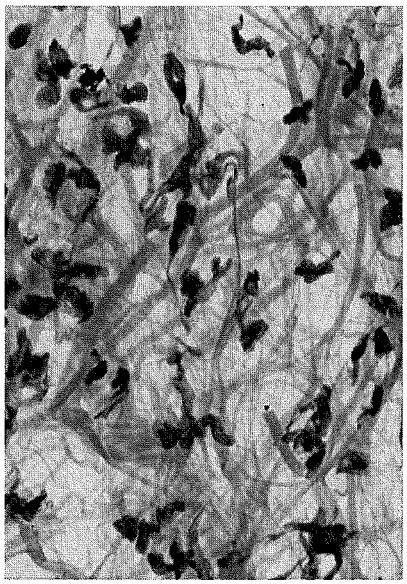
FIG. 22

FIG. 28
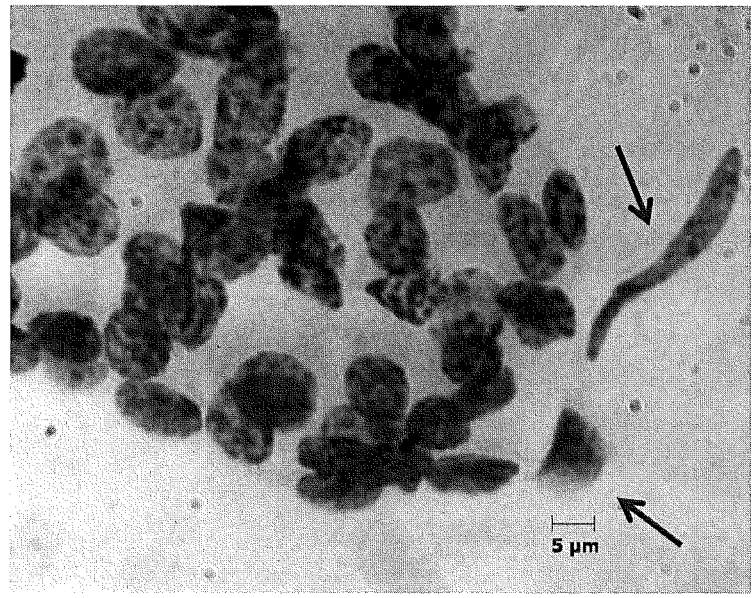
B
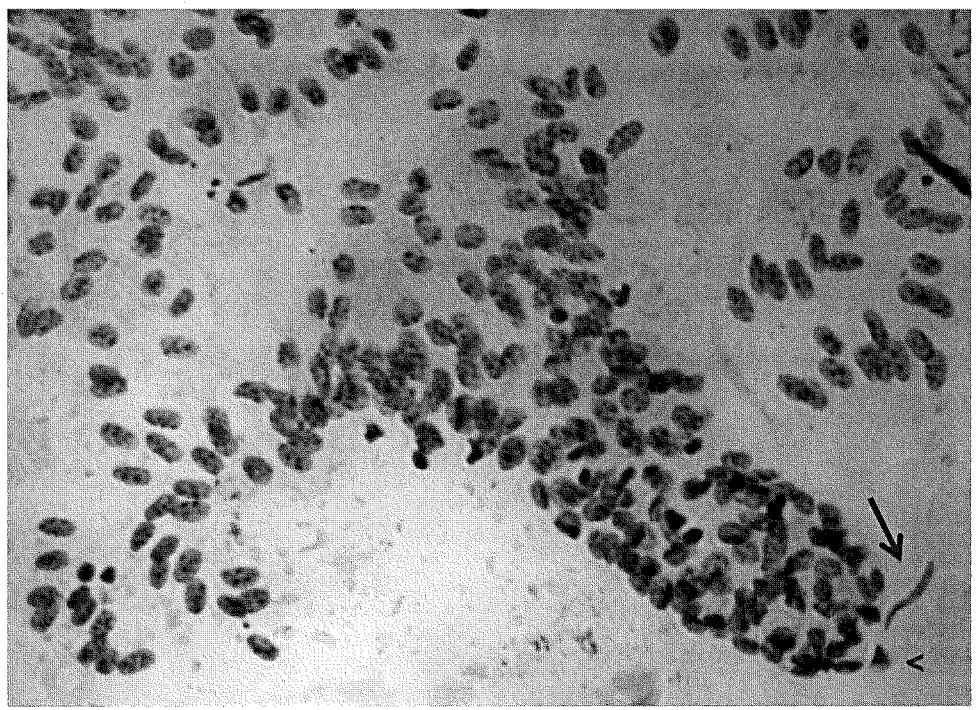
A

WOUND HEALING METAKARYOTIC STEM CELLS AND METHODS OF USE THEREOF

RELATED APPLICATION(S)

This application is the U.S. National Stage of International Application No. PCT/US2011/057513, filed Oct. 24 2011, which designates the U.S., published in English, and claims the benefit of U.S. Provisional Application No. 61/406,468, filed on Oct. 25, 2010. The entire teachings of the above applications are incorporated herein by reference.

BACKGROUND OF THE INVENTION

Wounds and wound healing disorders are pervasive and detract from the quality of life. Wounds that sever nerve communication result in paralysis. Wound healing disorders afflict wounds in organs and tissues after traumatic injuries and infection and equally include wounds and wound-like conditions following surgical interventions as is frequently required for vascular diseases arising from progressive disorders such as atherosclerosis. For example, vascular diseases, such as coronary or carotid artery disease, affect millions of individuals in the U.S. and many more worldwide. See, e.g., Ma et al., *J. Clin. Exp. Med.*, 3(3):192-201 (2010). Therapeutic intervention for vascular disease such as blood vessel transplantation, stents and angioplasty can ameliorate the debilitating effects of vascular disease by restoring normal blood flow. The improvements from these interventions may be only temporary, however, since wound healing disorders are commonplace and can give rise to complications such as restenosis, a re-narrowing of vessels following surgical intervention caused by a rapid increase in the number of smooth muscle cells of the vessel wall.

These novel observations relate directly to the debate in the art as to the identity and/or source of cells that give rise to wound healing lesions, such as those associated with blood vessel wound healing disorders such as post-surgical restenosis. Some authors have presented data that an undefined subset of the cells isolated from adventitia of aortic arches have certain stem cell-like properties (such as cell expression of cell surface markers) and a capacity to produce cells that may contribute to atherosclerosis. Hu et al., *J. Clin. Invest.*, 133(9): 1258-65 (2004). These studies of atherosclerosis are distinguished from the events of wound healing, such as post-surgical restenosis, described herein because the slow progression of atherosclerotic plaques over many decades is recapitulated in a matter of weeks and months in post-surgical restenosis. Restenosis has in fact been characterized as "galloping atherosclerosis." These studies do not establish a clear role for the specific cells studied in a disease state, let alone any morphological characterization of the cells to aid in their identification or classification, e.g., by microscopic examination by medical pathologists or histologists.

Other authors have described the distribution of cells with particular surface antigens and other characteristics, while characterizing the location of cells with possible stem cell like characteristics in vascular and/or vascular-proximate tissues. Unfortunately, it has been demonstrated that such antigenic markers or stem cells are widely distributed on and among cells that are not stem cells. Said markers are useful in enriching stem cells from cell mixtures but do not permit isolation and observation of stem cells specifically. See, Pasquinelli et al., *Cytotherapy*, 12:275-87 (2010). These studies, however, do not demonstrate a role for the cells with stem-like properties in any disease. In particular, Pasquinelli et al., did not observe symmetric or asymmetric amitoses of metakaryotes in vascular walls and did not observe creation of smooth muscle cells by asymmetric amitoses of metakaryotic cells. Accordingly, there is a need to identify cell types involved in wound healing and wound healing disorders. In addition, there is a need to identify agents to treat wound healing disorders by modulating growth and/or migration of cells involved in wound healing—i.e., stem cells involved in actual disease states. There is a further need for methods to identify agents to treat wound healing disorders characterized by aberrant excess tissue generation—e.g., by killing and/or slowing the migration, increase or production of differentiated cells for stem cells underlying the pathological disorders. This is particularly true for smooth muscle cells in the case of post-surgical restenosis

SUMMARY OF THE INVENTION

The present invention provides, inter alia, methods for recognizing the metakaryotic stem cells of wound healing and in wound healing disorders, such as post-surgical restenosis, as well as methods of identifying molecules to treat such wound healing disorders. The invention is based, at least in part, on the discovery of metakaryotic cells with bell-shaped nuclei increasing by symmetric amitoses and creating smooth muscle cells by asymmetrical amitoses in a restenotic lesion surgically derived from a transplant patient suffering from restenosis. It was also noted that smooth muscle nuclei did not further increase by either mitotic or amitotic fission processes. Smooth muscle cells rose one-at-a-time—from asymmetric amitoses of metakaryotic stem cells themselves increasing in/on the vessel luminal walls. This finding was in accord with similar observations of metakaryotic stem cells dividing by symmetric and asymmetric amitosis creating smooth muscle cells during development of the kidney artery of human fetuses. See FIGS. 2-4. The source of the metakaryotic stem cells in the restenotic lesions was suggested by the separate discovery by Applicants of metakaryotic cells in a non-dividing, quiescent state in the mesenchymal tissue areas of colons and other organs of adult mice and humans in numbers and cytological positions associated with adult mesenchymal stem cells. From these observations the Applicants concluded that metakaryotic adult stem cells of the adventitial tissue layers associated with the surgically joined blood vessels entered the wound, promote initial healing but inexplicably continued to increase in number and increase the number of smooth muscle cells until a pathological state of restenosis resulted.

In one aspect, the invention provides methods of identifying the stem cells of wound healing generally by recognition of cells and/or syncytia with bell-shaped nuclei actively dividing by both symmetric and asymmetric amitoses. Examples include the rapid appearance of metakaryotic cells at wound edges after corneal transplants and the appearance of metakaryotic tubular syncytia during healing of skeletal muscle wounds.

In a further aspect, the invention provides methods of identifying wound healing metakaryotic stem cells (also referred to herein as adult mesenchymal-associated metakaryotic stem cells) in a non-dividing state distributed widely in mesenchymal areas of tissues throughout the body. Such recognition permits specific physical isolation, e.g., laser-capture, of adult mesenchymal stem cells without reliance on relatively non-specific methods such as recognition with antibodies that attach inter alia to non stem cell types and masses of intercellular material.

Accordingly, in another aspect, the invention provides methods for diagnosing a wound healing disorder as a pathology related to misregulated growth and differentiation driven by the symmetrical and asymmetrical divisions of metakaryotic stem cells. An example of such a disorder is the blood vessel wound healing disorder known as post-surgical restenosis. The methods include the step of visualizing the nuclei of cells in an isolated tissue sample. The tissue sample is prepared by a method that fixes the physical structures of the DNA-containing cell nuclei so that their shapes may be recognized by subsequent microscopic examination. In some embodiments, the preparation method substantially preserves the integrity of nuclear structures in nuclei having maximum diameters up to about 50 microns. The methods also include the step of determining the presence and/or absence of cells with heteromorphic nuclear morphotypes in the tissue sample. In the case of restenosis the methods optionally include the recognition of increasing numbers of smooth muscle cells with their characteristic irregular nuclear forms and amitotic fissions showing creation of smooth muscle cells with identical sets of irregular nuclei by asymmetrical amitoses from metakaryotic cells. See FIGS. 9-13, 14A and 15-17. In lesions other than post-surgical restenosis the presence of cells with certain heteromorphic nuclear morphotypes associated with the normal tissue arising from metakaryotic stem cells by asymmetric amitoses is indicative of a wound healing disorder based on uncontrolled divisions of metakaryotic stem cells. In one embodiment, the cells driving the wound healing disorder are large, bell-shaped metakaryotic nuclei found to serve as the stem cells of human organogenesis and carcinogenesis (Gostjeva et al., *Organogenesis,* 5:4, 191-200 (2009); Gostjeva et al., *Cancer Genetics and Cytogenetics,* 14:16-24 (2006)). In another embodiment the metakaryotic cells create, via asymmetrical amitoses, the closed eukaryotic nuclei characteristic of the tissue in which the wound healing progressed to a pathologic lesion. In particular embodiments, the metakaryotic stem cells are actively dividing. In more particular embodiments, the metakaryotic stem cells are undergoing amitotic divisions. In still more particular embodiments, the amitotic division is a symmetrical amitotic division. In other more particular embodiments, the amitotic division is an asymmetrical division.

In certain embodiments, the wound healing disorder is a blood vessel wound healing disorder, such as injury-induced neointimal hyperplasia, post-anastomatosis complications or restenosis.

In more particular embodiments of the foregoing aspects of the invention, the blood vessel wall disorder is restenosis.

The tissue samples used in the methods provided by the invention may be physically (e.g., the sample is frozen) or chemically (e.g., treated with one or more chemical fixing agents selected from alcohols, aldehydes, organic acids and combinations thereof) fixed. In some particular embodiments, the tissue sample is fixed with a fixing agent comprising methanol and acetic acid. In certain embodiments, the tissue sample is fixed prior to cellular degradation of nuclei in the tissue sample (e.g., within about 20, 30, 40, 50, 60, 90, or 120 minutes of being isolated). In more particular embodiments, the tissue sample is fixed within 30 minutes of isolation and in still more particular embodiments, within 15 minutes of isolation. In some embodiments, the fresh, fixed or frozen cells of the tissue sample are partially dissociated by tissue maceration and spreading. In certain embodiments, the cells or macromolecules of the tissue sample are stained, thereby allowing visualization of nuclei. In more particular embodiments, the DNA is stained, thereby allowing visualization of the DNA and the nuclei. In some embodiments the cells are associated with fluorescence when stained under appropriate conditions. Gostjeva et al., 2006, 2009.

In certain embodiments of the invention, the tissue sample is obtained from a multicellular animal, such as a vertebrate. In more particular embodiments, the vertebrate is a mammal, such as a primate, rodent, canine, feline, porcine, ovine, bovine, or leporine. In still more particular embodiments, the mammal is a human. In some embodiments, the multicellular animal is deceased, i.e., the tissue sample is obtained post-mortem.

In particular embodiments, methods provided by the invention comprise the further step of visualizing heteromorphic nuclear morphotypes that include nuclei that are irregular, spindle-shaped, cigar-shaped, condensed-spherical, spherical, oval, sausage-shaped, kidney-shaped, bullet-shaped and combinations thereof. In more particular embodiments, the heteromorphic nuclear morphotypes are the bell-shaped nuclei of the metakaryotic stem cell nuclei and the characteristic irregular nuclei of smooth muscle cells. See FIGS. 9B and 13A-C. The term "irregular" here means to characterize the several morphological forms of smooth muscle nuclei that may resemble worm-like bodies (FIGS. 9B, 13C) or twisted forms (FIGS. 13A-C).

In certain embodiments, the methods of the invention can include the step of determining the spatial and/or numerical distribution of heteromorphic nuclear morphotypes within the tissue sample. In these embodiments, the spatial and/or numerical distribution of heteromorphic nuclear morphotypes further characterizes the tissue sample. In certain embodiments, the heteromorphic nuclear morphotypes are contained in multinuclear syncytia or in mononuclear cells. In some embodiments the heteromorphic nuclear morphotypes are bell-shaped nuclei and in more particular embodiments, the bell-shaped nuclei are associated with structures indicative of amitotic symmetrical nuclear division. In some embodiments the heteromorphic nuclear morphotypes are bell-shaped nuclei and in more particular embodiments, the bell-shaped nuclei are associated with structures indicative of amitotic asymmetrical nuclear division.

The invention also provides methods of identifying one or more agents to treat a wound healing disorder, such as a blood vessel wound healing disorder, e.g., by 1) stopping unwanted stem cell activity or 2) promoting certain stem cell activity. For example, said agents might act by inhibiting the migration from mesenchymal tissue areas, symmetric amitoses and/or asymmetric amitoses of the wound healing metakaryotic stem cells aberrantly creating the wound healing disorder.

Said inhibition of metakaryotic amitoses might be accomplished by holding the metakaryotes in a non-dividing state, causing them to leave the wound area or by killing the metakaryotic cells involved in the aberrant growth of the wound healing disorder as in the case of post-surgical restenosis. In a more particular embodiment said inhibition of metakaryotic amitoses is accomplished by exposure to a test agent at concentrations and durations sufficient to kill all metakaryotic cells involved in the wound healing disorder.

These methods include the step of treating a mammal having a wound or wound healing disorder, such as a blood vessel wound healing disorder, with a candidate agent and subsequently determining the numbers and forms of nuclear morphologies of cells contained within an isolated tissue sample comprising the relevant tissue and wound, e.g., blood vessel wall from the mammal. The methods further include the step of comparing the numbers and nuclear morphologies of the cells within the tissue sample from the mammal treated with the candidate agent with cells contained within an isolated tissue sample from a mammal having a wound healing disorder but not treated with the candidate agent. Relative to wounds in untreated or sham treated mammals halting of the increase, reduction or elimination of metakaryotic stem cells in the area of the wound healing disorder or a halting of the increase of smooth muscle cells by asymmetric amitoses of metakaryotic stem cells in the specific case of post-surgical restenosis would recognize a potentially valuable therapeutic agent. In some embodiments, the mammal treated with a candidate agent is an experimental animal such as a pig, dog, or rodent and in more particular embodiments, the rodent is a rat, mouse, or guinea pig. In certain embodiments, the metakaryotic bell shaped nuclei are arranged in multinuclear syncytia and the elimination of metakaryotic stem cells is associated with a disruption, disappearance or death of the syncytia.

In another aspect, the invention provides in vitro methods of identifying one or more agents to treat (e.g., by modulating proliferation and/or migration of metakaryotic stem cells) a wound healing disorder, such as a blood vessel wall disorder. The methods comprise contacting cultured cells comprising metakaryotic stem cells and cells normally present in the tissue of the wound such as smooth muscle cells in the case of post-surgical restenosis with one or more candidate agents at defined concentrations and durations of exposure and subsequently evaluating the numbers and nuclear morphologies of the cultured cells. A change in the growth or the number of metakaryotic stem cells as compared to control cell cultures not contacted with the candidate agent indicates the effectiveness of the agent to treat a wound healing disorder, such as a blood vessel wound healing disorder. In still more particular embodiments, recognition of a potentially valuable therapeutic agent in cell culture further comprises observation of ceased change in activity of metakaryotic stem cells in asymmetrical amitosis giving rise to cells associated with wound healing pathology such as cells with irregular nuclei characteristic of smooth muscle cells in the specific case of post-surgical restenosis.

In another aspect, the invention provides in vitro methods of identifying one or more agents to treat (e.g., by modulating proliferation and/or migration of metakaryotic stem cells) a wound healing disorder, such as a blood vessel wall disorder. The methods comprise contacting cultured cells comprising metakaryotic stem cells derived from mammalian fetuses or tumors with one or more candidate agents at defined concentrations and durations of exposure and subsequently evaluating the numbers and nuclear morphologies of the cultured cells. A change in the growth or the number of metakaryotic stem cells as compared to control cell cultures not contacted with the candidate agent indicates the effectiveness of the agent to treat a wound healing disorder, such as a blood vessel wound healing disorder. In still more particular embodiments, recognition of a potentially valuable therapeutic agent in cell culture further comprises observation of ceased change in activity of metakaryotic stem cells in asymmetrical amitosis giving rise to cells associated with wound healing pathology such as cells with irregular nuclei characteristic of smooth muscle cells in the specific case of post-surgical restenosis.

A further aspect of the present invention provides methods to treat a wound by recognition of mesenchymal metakaryotic stem cells, enriching them by recognition of their characteristic bell shaped nuclei to concentrate them, or increasing their number by growth in vitro and seeding them in the wound area. Said metakaryotic stem cells for transplant therapy might be obtained from the patient, an immunologically matched human donor, an unmatched human donor or from a non-human animal. Said metakaryotic stem cells for transplant therapy might be expanded in cultures prior to use in stem cell transplant therapy.

A further aspect of the present invention provides methods to recognize a test molecule that provokes a superior wound healing host response by modulating the migration, symmetric amitoses and or asymmetric amitoses of the wound healing stem cells.

As a result of Applicant's invention described herein, methods are now available to recognize, isolate and study the wound healing metakaryotes (adult stem cells) waiting for recruitment (e.g., "on call"), during recruitment (e.g., migration) and during wound healing (e.g., proliferation) from the mesenchymal areas of tissues generally, and from the mesenchymal adventitia of blood vessels specifically, as in the case of post-surgical restenosis.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 2A-C are micrographs showing syncytial structures in human fetal kidney artery (9 wks) with bell-shaped nuclei (arrowed). FIG. 2A is a Single bell-shaped nucleus with recognizable 'ring' of chromatin. FIG. 2B is a Symmetrical (bell-to-bell) nuclear fission. FIG. 2C is a Syncytial bell-shaped nuclei (arrowed), Feulgen (purple) and Feulgen (green) fluorescence merged image (×20).

FIG. 4A shows a form of asymmetric amitosis in which a metakaryotic bell shaped nucleus gives rise to a spherical nucleus such as are found in vessel endothelial cells along with an artists depiction of the process. FIG. 4B shows the symmetric amitosis of a metakaryotic bell shaped nucleus that has just given rise to two bell shaped metakaryotic nuclei representing net growth of metakaryotic stem cells. FIG. 4C shows purple Feulgen stained nuclei (purple) with several bell shaped nuclei and several closed nuclei having different morphologies within the vessel wall. FIG. 4D is a fluorescent image of the field shown in FIG. 4C except that here fluorescence (green) created presumably by Feulgen Schiff's base reaction with unknown structures, possibly cytoplasmic saccharides, emanating from the bell shaped nuclei or existing alone in the vessel wall. FIG. 4E combines the images of FIGS. 4C and 4D showing both purple and green fluorescent Feulgen stained structures.

FIG. 5A is a micrograph showing what the myotubes (arrows) of regenerating mammalian skeletal (striated) muscle look like under the microscope. They closely resemble the myotubes found in embryonic muscle. FIG. 5B is a micrograph showing myotube (arrow) in human fetal skeletal muscle, 9 wks. FIGS. 5C & D are micrographs showing bell-to-bell nuclear fission in human fetal myotube, muscle 9 wks.

FIG. 6A is a micrograph showing that in normal non-diseased human artery (fraction of cells with bell-shaped nuclei (in a child) is low ~$1\times10^{-4}$-$1\times10^{-5}$). FIG. 6B is a micrograph showing asymmetric nuclear fission 'Stem cell-Smooth muscle cell' (arrow). FIGS. 6C, D are micrographs showing that bell-shaped nuclei (arrowed) are rare (~$1\times10^{-5}$) in young adult pig pulmonary artery.

FIG. 7 shows a series of micrographs of normal non-diseased heart and failed donor heart artery of child's heart (2 YRS). FIG. 7A shows an example of a sample used to determine that the fraction of metakaryotic cells is ~$1\times10^{-5}$ in normal heart. FIG. 7B shows an example of a sample used to determine that the fraction of metakaryotic cells in plaque is ~$1\times10^{-4}$ in failed donor heart. FIGS. 7C, D, and E are micrographs showing right (and left) ventricles cardiomyocytes in a transplanted heart were contaminated by cocci bacteria. The fraction of metakaryotic cells was found to be ~$2\times$ in $10^{-4}$ in such contaminated tissue surfaces.

FIG. 9 shows a pair of micrographs showing fibronectin in a biopsy from a patient suffering from post-transplant restenosis. Here FIG. 9A shows the nascent fibronectin fibers associated both with bell shaped metakaryotic nuclei and nuclei of smooth muscle cells with a characteristic set of irregular nuclei. FIG. 9B shows a thick mat of fibronectin with one bell shaped nucleus and several irregularly shaped nuclei of smooth muscle cells.

FIG. 10 shows a pair of micrographs showing calcification in a biopsy from a patient suffering from post-transplant restenosis. FIG. 10A shows calcification along fibronectin fibers, while FIG. 10B, at higher magnification, reveals several bell shaped nuclei that are generally distributed throughout the plaques.

FIG. 15 shows a series of micrographs of in a biopsy from a patient suffering from post-transplant restenosis. FIG. 15A shows fibronectin fibers associated with bell shaped and other shapes of nuclei. FIG. 15B shows the result of recent asymmetrical amitosis in which a bell shaped nucleus appears to have given rise to a nucleus or nuclei with morphologies of smooth muscle cells. FIG. 15C shows two bell shaped nuclei immediately adjacent to two nuclei of smooth muscle cells. FIG. 15D captures what appears to be a recent asymmetrical amitosis from the bell shaped metakaryotic stem cell nucleus on the left to create an almost spherical nucleus from which fibronectin appears to originate.

FIGS. 22A-C are micrographs illustrating the following: FIG. 22A shows normal pulmonary vein without metakaryotic cells; FIG. 22B shows stenotic right and left pulmonary vein with numerous metakaryotic cells; FIG. 22C shows confluence of anastomosis with numerous metakaryotic cells.

FIG. 23C shows the shape of a smooth muscle cell nucleus after emerging from asymmetric amitoses of a metakaryotic stem cell (blow up).

FIG. 28 provides micrographs of mouse colon. FIG. 28A Shows a whole crypt of ~256 cells in mouse ascending colon. FIG. 28B shows a magnified part of the base of this crypt showing bell-shaped metakaryotic stem nucleus at the base of the crypt (red arrow) and characteristic irregular nucleus of smooth muscle cell (blue arrow) from separate supporting stromal layer. Feulgen DNA staining (purple). See Gostjeva et al., 2006.

FIGS. 32A-B are micrographs of bladder tissue. FIG. 32A shows branching blood vessel in normal bladder of 4 years old child: Metakaryotic stem cell with bell-shaped nucleus (red arrow), smooth muscle cells with irregular nuclei (blue arrows) and blood cells (green arrows). Feulgen DNA staining (purple).

DETAILED DESCRIPTION OF THE INVENTION

Figure 1:
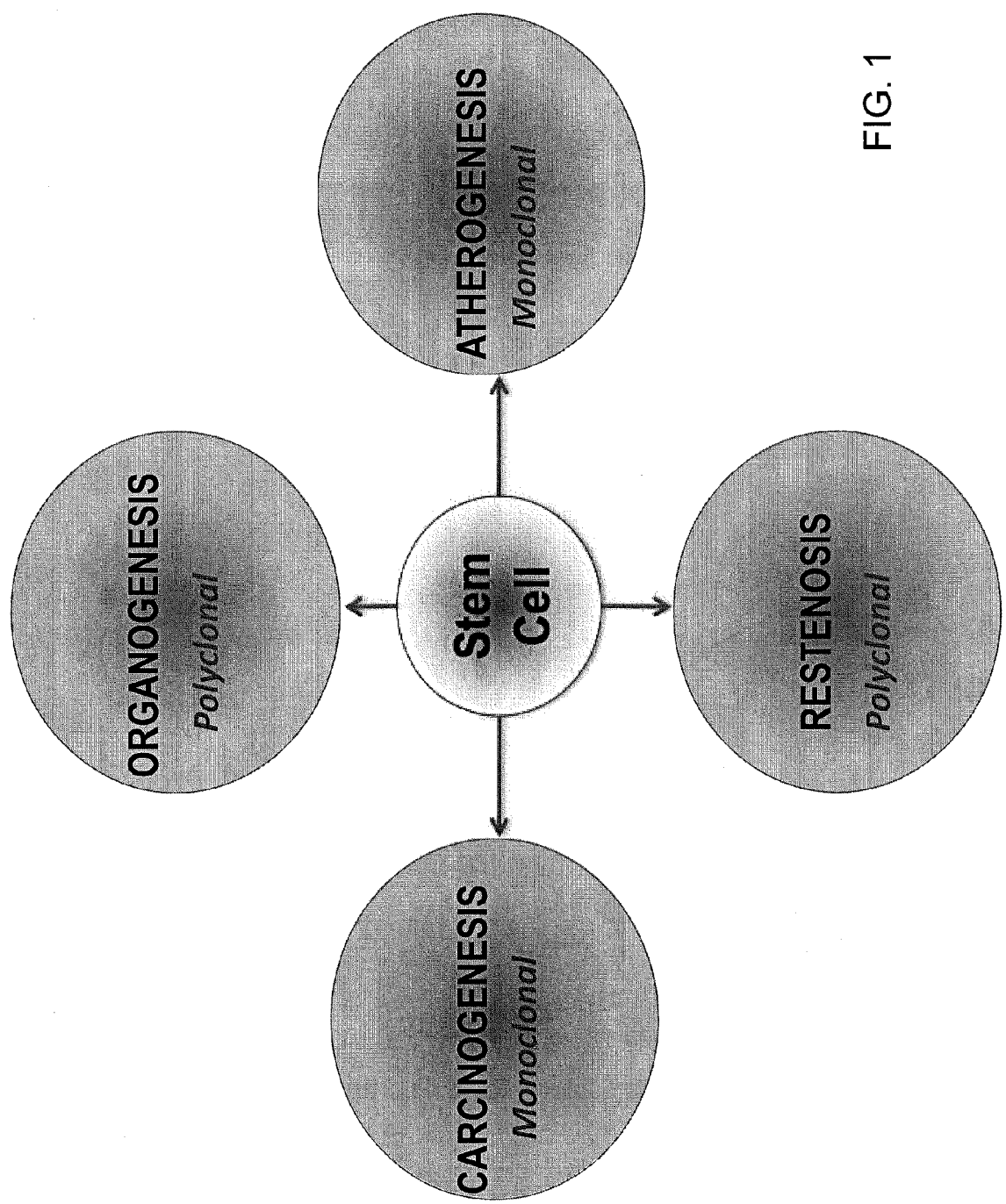
FIG. 1 illustrates roles of metakaryotic stem cells of normal development and important pathological conditions.

A description of example embodiments of the invention follows. The invention reported here is based, in part, on the discovery of adult metakaryotic stem cells with bell-shaped nuclei 1) in a non-dividing quiescent state in the mesenchymal tissue areas of colons and other organs of adult mice and humans in numbers and cytological positions associated by others with adult mesenchymal stem cells, 2) dividing by symmetric and asymmetric amitoses creating the smooth muscle cells of the primary kidney artery of human fetuses and 3) dividing rapidly by symmetric and asymmetric amitoses to create to increase the number of metakaryotic and smooth muscle cells in the vicinity of a vascular ligature in a heart transplant patient suffering from lethal, post-surgical restenosis. These discoveries joined with previous discoveries of applicants provide a simple paradigm in which the metakaryotic stem cells of tissue mesenchyme (variously named, undifferentiated tissue, stroma, adventia et alia) serve as the stem cells of wound healing and the derived pathological conditions such as untoward increases in smooth muscle cells in the clonal disease atherosclerosis and the polyclonal condition of post-surgical restenosis. The invention provides methods of diagnosis and study of wound healing disorders such as, for example, restenosis by means including, for example, histopathological methods. Additionally, the invention provides both in vitro and in vivo methods to identify agents that either stimulate or inhibit proliferation of adventitia-associated metakaryotic stem cells.

Applicants had previously discovered that the developmental expansion of many fetal organs involved a stem cell lineage comprised of syncytia (multinuclear cells) and mononuclear cells in which each nucleus had a hollow bell shape. These cells did not use mitosis in nuclear division but divided without chromosome condensation, a method of division termed "amitosis." Net growth of these bell shaped nuclei was accomplished by symmetric amitoses in which one bell shaped nucleus divided to form two bell shaped nuclei of identical shape and each containing the entire DNA complement of diploid human cells. These cells accomplished the steps necessary for cellular differentiation in fetal development by the process of asymmetric amitoses in which a bell shaped nucleus divided by amitosis to yield a new hollow bell shaped nucleus and a closed nucleus. Cells with these closed nuclei subsequently increased in cell number by successive mitotic divisions such that these mitotic cell types became the vast majority of parenchymal cells of each tissue and organ. Interestingly, in both symmetric and asymmetric amitoses of bell shaped nuclei the genomic complement of DNA was not doubled prior to nuclear divisions but during and somewhat after this process was complete. Because these cells with bell shaped nuclei did not have the characteristics of "eukaryotic" cells that replicate their DNA some hours prior to chromosome condensation and nuclear division, they were denominated as a novel cellular class, "metakaryotes." Because they were identified as the source of parenchymal mitotic cells during development of organs, and, importantly, their derived tumors, the metakaryotic cells were identified as stem cells comprising an important part of the stem cell lineage between a fertilized ovum and the differentiated cells of an adult animal or plant. See Gostjeva, et al. 2005, 2006, 2009.

Having established that the growth and differentiation processes of organogesis and carcinogenesis were driven by metakaryotic cells, Applicants turned to other diseases in which cell growth and differentiation occur simultaneously, among which are the processes of wound healing and related phenomena of tissue regeneration.

The invention provides methods of diagnosis of wound healing disorders such as, for example, restenosis. Additionally, the invention provides both in vitro and in vivo methods to identify agents that inhibit proliferation of adventitia-associated metakaryotic stem cells.

In humans, the metakaryotic stem cells with bell shaped nuclei are first observed in the fourth and fifth week post-fertilization, apparently rising from a different form of amitosis of precursor mitotic embryonic stem cells. At this time metakaryotic cells increase in multinuclear syncytia that are distributed in radial-spherical clusters nonrandomly throughout early developing organs. At and about twelve weeks of gestation the syncytia dissolve and all metakaryotic nuclei are found in niches expected of organogenic stem cells throughout fetal and juvenile development, for instance, in the colonic crypts. Single mononuclear metakaryotic cells are found only in the very lowest position at the base these crypts. At some time before or at organ maturity metakaryotic nuclei give way to mitotic "maintenance" stem cells that divide to replace tissue cells that undergo normal "programmed" death found in nearly all tissues. Gostjeva et al., 2009.

Apprised of the medical importance of post-surgical restenosis, Applicants sought to understand the cascade of cellular divisions creating these life-threatening and often lethal processes. In their studies of human organs and tumors a relatively few metakaryotic stem cells gave rise to several different types of eukaryotic cells that subsequently created the mass of the organ by a series of binary mitotic cell divisions. The growth rate of such organs or tumors could be gauged by the difference in the frequency of mitoses corrected for the number of cells undergoing programmed cell death by the process of apoptosis.

However, during the increase in smooth muscle cells in post-surgical restenosis such dividing mitotic smooth muscle cells were not observed. Thus the means of smooth muscle cell increase was unclear. However, Applicants identified cells with bell shaped nuclei undergoing symmetrical amitoses (net growth of metakaryotic cells) and asymmetric amitoses that inter alia created nuclei in the form of irregular forms characteristic of smooth muscle cells. See FIGS. 9-13, 14A, 15, 16 and 17. In contradistinction to all developing tissues and their derived tumors, the smooth muscle nuclei created by metakaryotic amitoses in restenotic lesions did not further divide but seemed to be increased solely by the action of the metakaryotic cells, i.e., they were increased one cell at a time from the immediate metakaryotic precursors.

The discovery that smooth muscle cells are created by asymmetric amitoses of metakaryotic stem cells offered an explanation of two puzzling and contradictory observations about the behavior of smooth muscle cells in post-surgical restenosis and other wound healing phenomena. Smooth muscle cell numbers are universally reported to increase in number both slowly as in atherosclerotic plaques and rapidly as in post-surgical restenosis but no reports exist that they increase by division of smooth muscle cells by either mitotic or amitotic mechanisms. However, when human or experimental animals were treated with biochemical precursors specific for DNA such as tritiated thymidine or bromodeoxyuridine the nuclei of many smooth muscle cells were observed to have taken up these specific DNA precursors in a stable form, i.e. DNA. These observations were used by many scientists to conclude that smooth muscle cells actively divided. However, the smooth muscle cells as noted above have not been found to undergo cell division by mitosis or amitosis after careful study by Applicants. Other findings of Applicants can now explain this apparent contradiction.

First is their demonstration that smooth muscle cells arise specifically from metakaryotic cells and not from division as smooth muscle cells explains the absence of observation of dividing smooth muscle cells. The metakaryotic cells thus increase in wound healing by symmetric amitotic divisions as they do in organogenesis and carcinogenesis. Secondly, Applicants have discovered that metakaryotic stem cells do not use the mode of DNA replication used by prokaryotic and eukaryotic cells in which the DNA double helix is first replicated in the form of two double stranded DNA helices and then segregated in two daughter cell nuclei. Instead, as described in U.S. provisional patent application No. 61/492,738, filed Jun. 2, 2011, Applicants have discovered that metakaryotic stem cells first create two pangenomic copies of their genomes as double stranded RNA/DNA heteroduplexes and it is these dsRNA/DNA replicative intermediates that are segregated into derived daughter nuclei by asymmetrical amitosis of metakaryotic stem cells of the restenotic lesions. After segregation the dsRNA/DNA is converted to a canonical dsDNA helical form by a process that includes degradation of the RNA pangenomic copy and subsequent copying of the single DNA strand in each daughter cell. Thus a non-dividing smooth muscle cell will take up tritiated thymidine or bromodeoxyuridine or other specific DNA precursor, even though it will not subsequently divide. These findings explains the paradox of uptake of DNA precursors into the DNA genomes of non-dividing smooth muscle cells. It is the copying of the single DNA strand of the dsRNA/DNA replicative intermediate of the smooth muscle genome that created the appearance of DNA doubling when it was caused by DNA copying post segregation in a cell that did not subsequently divide. The apparent "proliferation" of smooth muscle cells in rapid post-surgical restenosis is thus taught to be the result of proliferation of metakaryotic stem cells that create non-dividing smooth muscle cells "one-at-a-time" by asymmetric amitotic divisions.

Furthermore Applicants' studies of multiple organs in adults, particularly the colons of humans and mice, found non-dividing metakaryotic cells widely distributed in the non-epithelial portions of tissues associated with the relatively disorganized mesenchymal tissue elements or "adventitia," a tissue niche suggested by many authors as the place of residence of adult mesenchymal stem cells "on call" for wound healing. Similar niches abundant in metakaryotic cells may be found as the "undifferentiated mass," "adventitia", "mesenchyme" or "stroma" of human tumors. Such niches are often noted to be "mucinous" a quality associated by Applicants to the mucinous material that is abundantly found in the non-nuclear "cytoplasmic organelle" of metakaryotic cells to which the bell shaped nuclei are attached.

In addition, Applicants noted that the field of stem cell transplants to heal the a wide variety of wounds has depended on isolation of mixtures of tissue cells undefined with regard to the number and identity of stem cells hypothetically contained therein. Their discovery of the metakaryotic cell forms distributed throughout the body in mesenchymal tissue areas offers a method to specifically identify and isolate metakaryotic wound healing stem cells for use in patient treatment without dilution or inhibition from non-stem cells abundantly present in mesenchymal extracts "enriched" for unidentified stem cells.

Applicants teach that methods to increase and enumerate living metakaryotic stem cells will in many cases be required for stem cell transplant therapy, for determining which drugs and which concentrations of such drugs are effective in promoting the growth of metakaryotic stem cells required for such therapy in vivo, and for determining which drugs and which concentrations of such drugs are effective in killing metakaryotic stem cells responsible for wound healing disorders such as postsurgical restenosis.

Applicants note that successful use of mesenchymal metakaryotic stem cells isolated on the basis of their specific morphology will in some cases be sufficient to initiate and promote wound healing but in other cases may require larger numbers of stem cells for successful therapy. To this end they teach that metakaryotic cells from a tissue or tumor may be grown in laboratory cell cultures until a number of metakaryotic stem cells is created sufficient or therapeutic purposes. While methods generally employed in cell culture may ostensibly be employed Applicants have observed rapid growth of metakaryotic cells in cell culture conditions not generally practiced in research laboratories designed by them to permit facile expansion of metakaryotic cell numbers. In particular while using any of a number of basic recipes for cell culture media, e. g. MEM, BME, DMEM, they have modified these recipes by replacing glucose with fructose (5-10 mM), omitting added sodium bicarbonate entirely; said media with fructose (or other non-glucose saccharide such as galactose) they teach are employed in the presence of air alone and not as generally practiced in the presence of air mixed with carbon dioxide, e.g., a mixture of 5% carbon dioxide with 95% air.

Metakaryotic Cells

Metakaryotic cells exhibit a striking, yet only recently recognized nuclear morphotype: a hollow, bell-shaped nucleus. For a review, see, Gostjeva and Thilly, *Stem Cell Reviews* 2: 243-252 (2005); see also FIGS. 1, 2, 3, 6 and 7 from U.S. Pat. No. 7,427,502 and their descriptions, which are also incorporated by reference. These cells also undergo both symmetric (giving rise to additional bell-shaped nuclei) and asymmetric (giving rise to non-bell-shaped nuclei) "amitoses"—division without mitosis and associated chromosome condensation. Through these amitoses, metakaryotic cells can give rise to heteromorphic nuclear morphotypes that populate the parenchyma of developing tissues, preneoplastic lesions and tumors including bell-shaped, cigar-shaped, condensed-spherical, spherical, oval, sausage-shaped, kidney-shaped, bullet-shaped, irregular spindle-shaped, and combinations thereof. See, e.g., FIG. 1 and from U.S. Pat. No. 7,427,502. "Metakaryote," "metakaryotic cell," "metakaryotic stem cell," "wound healing metakaryote" and the like, refer to a cell with a hollow, bell-shaped nucleus, where the cell divides by amitosis—either symmetrical or asymmetrical amitosis.

The skilled artisan will be able to readily identify metakaryotic cells when practicing the methods provided by the invention. For example, the methods of screening, diagnosis, and treatment provided herein can comprise the step of detecting metakaryotic cells from a tissue sample or in cultured cells. Cultured cells or cells from within a tissue samples being visualized by the methods of the invention are prepared in a way that substantially preserves the integrity of nuclear structures in nuclei having maximum diameters up to about 10, 20, 30, 40, 50, 60, or 70 microns—and in more particular embodiments up to about 50 microns. Methods for preparing cells are also described in U.S. Pat. No. 7,427,502, the teachings of which are incorporated herein by reference in their entirety. In certain embodiments, the preparation substantially preserves the integrity of nuclear structures in nuclei of about 10-15 microns. For example, in some embodiments a tissue sample may be analyzed as a preparation at least about 20, 30, 40, 50, 60, 70, 80, 90, 100, 150, 200, 250, 300, 350, 400, 450, 500, 750, 1000, 1250, 1500 or more microns in thickness. In certain embodiments, a tissue sample is macerated by, for example incubation in a solution comprising about 45% acetic acid in preparation for analysis.

In some embodiments, to further facilitate detection of metakaryotes, cultured cells or tissue samples can be stained. In particular embodiments, the staining can comprise staining with, for example, a Schiff's base reagent, Feulgen reagent, or fuchsin. In more particular embodiments, the tissue sample may be further stained with a second stain. In still more particular embodiments, the second stain may be Giemsa stain.

In certain embodiments, some but not all, metakaryotic cells can be detected by the fluorescence of their cytoplasm, following treatment with a non-fluorescent stain, such as Schiff's reagent. See, e.g., U.S. Patent Application Publication No. 2010/0075366 A1, including Example 5, FIGS. 20-27, and their descriptions, all of which are incorporated by reference. In the present invention "metakaryotic stem cells associated with wound healing disorders," "wound healing metakaryotes," and the like, include metakaryotic stem cells that do not exhibit large mucinous balloon-shaped cytoplasms, e.g., in postsurgical restenoses and other normal and pathological conditions such as development of the vascular tree, in addition to the large, mucinous balloon-shaped cytoplasms of the metakaryotic cells described in development of other organs and tissues, preneoplastic lesions and tumors, e.g., U.S. Patent Application Publication No. 2010/0075366 A1. Applicants teach specifically that the Feulgen fluorescence of metakaryotic stem cells involved in vasculogenesis and restenosis by creating smooth muscle cells show a different form of cytoplasmic staining including undetectable cytoplasmic Feulgen fluorescence.

In addition to their unique nuclear morphotypes and cell division, in some embodiments, metakaryotes can be further characterized but not distinguished by detecting particular marker genes. In particular embodiments, the marker genes can include one or more of CD133 (prominin 1; human GeneID 8842, reference mRNA and protein for the longest isoform are NM_006017.2 and NP_006008.1, respectively) and CD44 (human GeneID 960, reference mRNA and protein sequences for the isoform 1 precursor are NM_000610.3 and NP_000601.3, respectively. Use of these markers has been reported to be useful for enriching stem cells defined in end dilution xenotransplant assays from human tumors. Applicants teach that these two particular markers recognize antigens on the outside of metakaryotic cytoplasmic organelles in mononuclear metakaryotes but not any antigens in multinuclear metakaryotes in syncytial form. Applicants and a growing number of other researchers teach that antibodies directed to these two antigens further recognize certain eukaryotic cells and amorphous material found ubiquitously in cell culture and certain tissue samples. In other embodiments, markers for identifying and/or further characterizing metakaryotic cells, especially those undergoing cell divisions, include including DNA polymerase beta (human GeneID 5423), DNA polymerase zeta (human GeneID 5980), and RNAseH1 (human GeneID 246243). The marker gene may be detected at the nucleic acid (e.g., RNA) or protein level. In more particular embodiments, the marker genes may be detected at the periphery of a balloon-shaped cytoplasm of a metakaryote. The foregoing GeneIDs may be used to retrieve publicly-available annotated mRNA or protein sequences from the NCBI website. The information associated with these GeneIDs, including reference sequences and their associated annotations, are all incorporated by reference. Reference sequences from other organisms may readily be obtained from the NCBI website as well.

Metakaryotic cells may also be identified and/or quantified by detecting dividing metakaryotic cells, for example, by detecting an intermediate of an amitosis. Intermediates of amitosis include, for example, gross nuclear morphology (e.g., separating stacked cups, in the case of symmetrical amitosis) or by detecting a replicative intermediate comprising a single-stranded DNA (ssDNA) containing genome. For example, ssDNA can be detected using techniques that are standard in the art. A ssDNA containing replicative intermediate has previously been identified in metakaryotes following treatment to degrade RNA. See, International Publication Nos. WO 2008/156629 A2 (e.g., FIGS. 11-14, 17, and 18 and their descriptions) and WO 2007/067795, the teaching of both publications are incorporated by reference. Additional methods for identifying metakaryotes by the presence of an intermediate dsRNA/DNA duplex genome are described in U.S. provisional patent application No. 61/492,738, filed Jun. 2, 2011.

Diagnostic Methods

The diagnostic methods provided by the invention comprise determining (e.g., measuring) the presence and/or quantity and/or migration of metakaryotic cells in a tissue sample from a subject to diagnose a wound healing disorder in the subject. In a particular embodiment, the presence and/or quantity of dividing metakaryotic cells is determined.

I. Disorders

A "wound healing disorder" is a disease or disorder characterized by aberrant tissue generation during the repair of damage to tissues and/or organs following surgical intervention, recovery from infection (such as a flesh-eating infection), and/or acute trauma, where the aberrant tissue generation is non-cancerous and non-precancerous. In some embodiments, the wound healing disorder is characterized by aberrant excessive tissue generation. In other embodiments, the wound healing disorder is characterized by aberrant inadequate tissue generation. Exemplary wound healing disorders include blood vessel wound healing disorders, spinal cord wound healing disorders, wound healing disorders associated with organ transplants and wounds associated with traumatic injuries. In more particular embodiments, the wound healing disorder is post-surgical. Surgery, such as organ transplant (e.g., heart, liver, lung, cornea, et cetera) or surgical intervention, such as angioplasty, stent placement, et cetera, often leads to restenosis (arterial or veinous). Such restenosis is the frequent cause of death in transplant recipients. Acute traumas can include, for example, burns, cuts and gunshot wounds. The present invention provides the first experimental evidence that smooth muscle generation does not occur by canonical mitotic division, but rather by asymmetrical amitotic division from metakaryotic cells. Thus, although Applicants do not wish to be bound by theory, it is believed that wound healing disorders, such as blood vessel wound healing disorders—including restenosis—occur by smooth muscle generation, where the smooth muscle cells are produced by asymmetrical amitotic division of metakaryotic cells and not by division of smooth muscle cells. Applicants are aware that normal wound healing and other wound healing disorders, unlike post-surgical restenosis in blood vessels, may involve subsequent mitotic divisions of eukaryotic cells derived from wound healing metakaryotic stem cells in mononuclear and/or multinuclear, syncytial forms.

In some embodiments the wound healing disorder is monoclonal; i.e., the disorder arises by linear growth from a single metakaryotic cell vis-à-vis asymmetrical divisions to form an aberrant excessive tissue growth as in, for example, cancer and atherogenesis. In other embodiments, the wound healing disorder is polyclonal, i.e., the disorder arises from two or more metakaryotic cells by both symmetrical and asymmetrical divisions as in, for example, organogenesis and restenosis.

A "blood vessel wound healing disorder" is a wound healing disorder in vascular tissue, excluding atherosclerosis. In certain embodiments a blood vessel wall disorder is characterized by aberrant excessive smooth muscle generation and/or proliferation of metakaryotic cells in vascular tissue, particularly luminal surfaces, such as the intima. Exemplary blood vessel wound healing disorders include, for example, injury-induced neointimal hyperplasia and restenosis (e.g., following transplantation, stenting, anastomosis or trauma). In more particular embodiments, the blood vessel wall disorder is restenosis. In some embodiments, the blood vessel wall disorder occurs after surgery, infection, or acute trauma. In more particular embodiments, the blood vessel wall disorder is post-surgical.

"Restenosis" refers to a re-narrowing of an artery, typically by a thickening of the intimal surface, following surgical intervention such as angioplasty, stenting, or transplantation.

II. Subjects and Tissue Samples

Subjects to be diagnosed, screened, or treated by the methods provided by the invention include any multicellular animal, such as a vertebrate. In particular embodiments, the subject may be a mammal, such as a primate, a rodent, a canine, a feline, a porcine, an ovine, a bovine, or a leporine. In still more particular embodiments, the subject is a primate, e.g., a human.

The subject may be at any stage of development, e.g., a fetus, neonate, infant, child, adolescent, adult, or geriatric. In particular embodiments, the subject is a child, adolescent, adult, or geriatric. In still more particular embodiments, the subject is an adult or geriatric. In certain embodiments, the subject is at least about 1, 2, 3, 4, 5, 10, 20, 25, 30, 35, 40, 45, 50, 55, 60, 65, 70, 75, 80, 85, 90, 95, 100, 105 or more years old, e.g., about 1-5, 5-10, 10-20, 18-25, 25-35, 35-45, 45-55, 55-65, 65-75, 75-110, 80-110, 90-110, 95-110, or 100-110 years old, or greater and in still more particular embodiments, 100-104 years old. In certain embodiments, the subject is deceased, i.e., the method is a post-mortem diagnostic method.

In some embodiments, the subject is suspected of having a wound healing disorder. In more particular embodiments, the subject is suspected of having a blood vessel wound healing disorder.

In certain embodiments, the subject has previously undergone surgery. In more particular embodiments, the surgery is a stenting and/or balloon angioplasty. In still more particular embodiments, the subject has previously received more than one stent, e.g., at least 2, 3, 4, 5, or more stents. In these embodiments the stents may be drug-eluting (e.g., sirolimus or paclitaxel-eluting, including analogs thereof; rapamycin-eluting, including analogs thereof; as well as anti-CD-34 or anti-VEGF antibody-coated stents), non-drug-eluting, or combinations thereof.

In some embodiments, the subject has previously received a transplant, e.g., an allograft, autograft, or xenograft. In particular embodiments the subject has had a complete or partial organ transplant (e.g., heart, liver, kidney, bladder, skin, lung, or cornea transplant), or a valve or vessel transplant. The transplanted vessels may be either arteries and/or veins. In particular embodiments, the subject is suspected of having restenosis following surgery.

In certain embodiments, the tissue sample from the subject is obtained surgically, e.g., during a surgery such as a transplant, angioplasty, or stenting, or in a biopsy procedure. The tissue sample may include tissues such as, blood, vascular tissue, adipose tissue, lymph tissue, connective tissue (e.g., fascia, ligaments, tendons), adventitia, serosa, aponeuroses, endocrine tissue, mucosal tissue, liver, lung, kidney, spleen, stomach, pancreas, colon, small intestine, bladder, gonad, mammary tissue, central nervous tissue, peripheral nervous tissue, skin, smooth muscle, cardiac muscle, or skeletal muscle. In some embodiments a tissue sample may comprise 1, 2, 3, 4, 5, or more of the above tissues. In more particular embodiments a tissue sample may comprise or consist essentially of primarily one tissue, e.g., the tissue sample is about 10, 20, 30, 40, 50, 60, 70, 80, 90, 95, or 100% by weight of a single tissue. In more particular embodiments, the tissue sample comprises blood vessel tissue and in still more particular embodiments, blood vessel wall tissue. In some embodiments, the issue sample consists essentially of blood vessel tissue. In certain embodiments, the blood vessel tissue further comprises adventitia. In more particular embodiments, the blood vessel tissue consists essentially of adventitia and blood vessel tissue.

The tissue samples to be analyzed by the methods provided by the invention may be analyzed either fresh (e.g., in the absence of any fixation) or after physical or chemical fixation. Exemplary physical fixation includes freezing. Chemical fixation can use any fixative known to the skilled artisan, such as those comprising alcohols, aldehydes, organic acids and combinations thereof, so long as the chemical fixation preserves metakaryotic cells. For example, in particular embodiments, the chemical fixative comprises methanol and glacial acetic acid, and in more particular embodiments in a ratio of about 4:1, 3:1, 2:1, 1:1 methanol to glacial acetic acid.

To efficiently detect metakaryotic cells, tissue samples should be prepared to both preserve the heterogeneous nuclear morphotypes associated with metakaryotic cells (e.g., by fixing and/or visualizing soon after isolation from the patient to avoid degradation of the structures) and enable visualizing them efficiently (e.g., by providing relatively thicker histological preparations, as compared to typical 5 micron histological slices). The skilled artisan will readily be able to adapt the teachings of Examples 1 and 2 of U.S. Pat. No. 7,427,502 (which are incorporated by reference) to achieve this end. See also, Gostjeva et al., *Organogenesis,* 5:4, 191-200 (2009); Gostjeva et al., *Cancer Genetics and Cytogenetics* 14:16-24 (2006). Accordingly, in some embodiments, the cells of the tissue sample from the subject are visualized or fixed by the methods of the invention within about 1, 5, 10, 15, 20, 25, 30, 40, 50, or 60 minutes of being isolated from the subject.

In certain embodiments, the diagnostic or prognostic methods of the invention may further comprise the step of detecting particular non-metakaryotic cells, such as the irregular nuclei characteristic of smooth muscle cells, e.g., the methods my comprise a step of detecting smooth muscle cells, and in more particular embodiments, a change in the number of smooth muscle cells, i.e., an increase or decrease in the number of these cells.

Screening Methods

Figure 29:
FIG. 29 is a micrograph showing supporting stroma in adult ascending mouse colon devoid of crypts: Blue arrows indicate nuclei of smooth muscle cells and red arrows indicate metakaryotic stem cells with bell-shaped nuclei in mesenchymal part underlying epithelial part (crypts—cells to the right, black arrow) of colon.
Figure 30:
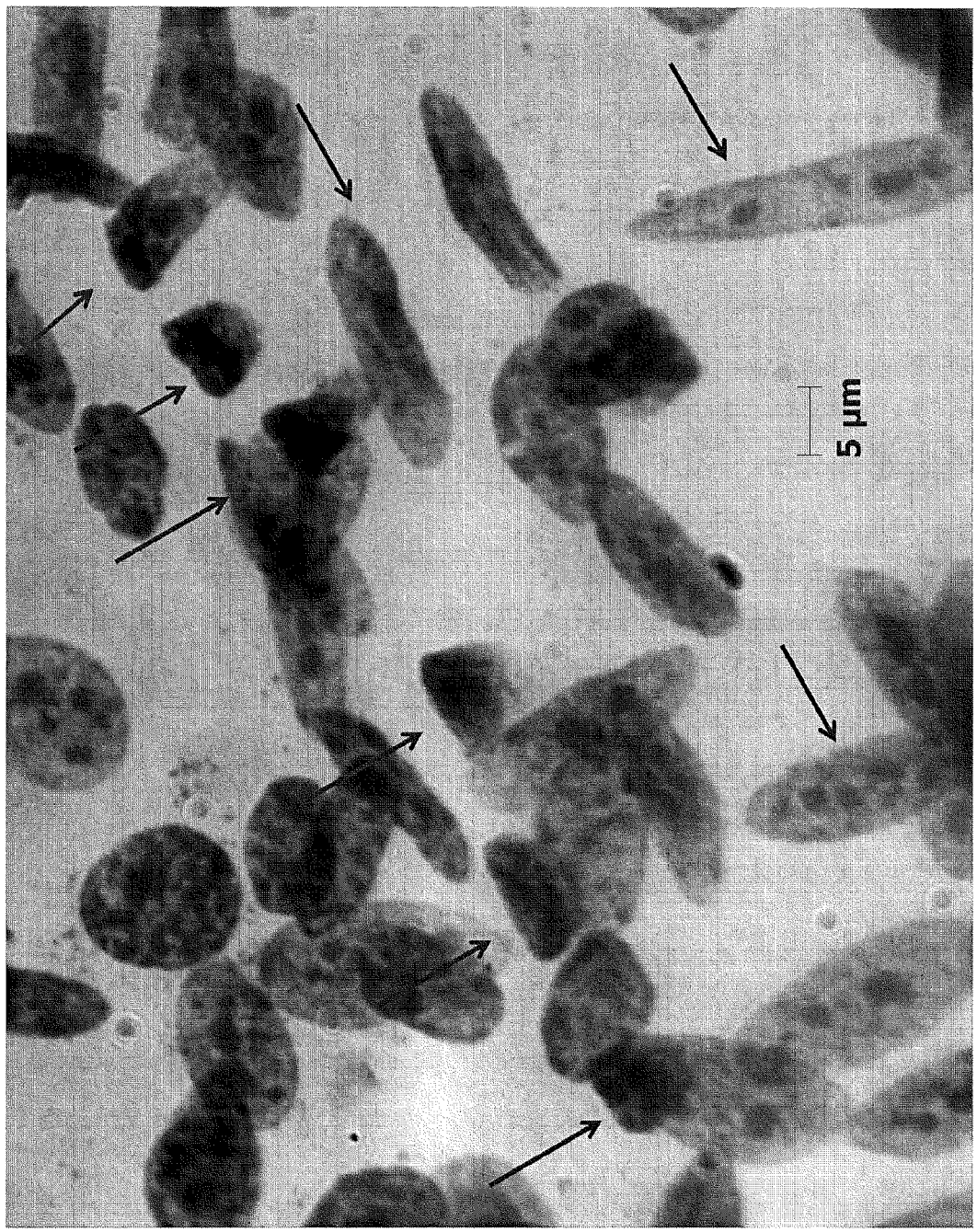
FIG. 30 is a ×100 micrograph image of metakaryotic stem cells (red arrows) and irregular nuclei of smooth muscle cells (blue arrows) in mesenchymal part of adult mouse ascending colon. Feulgen DNA stain.
Figure 31:
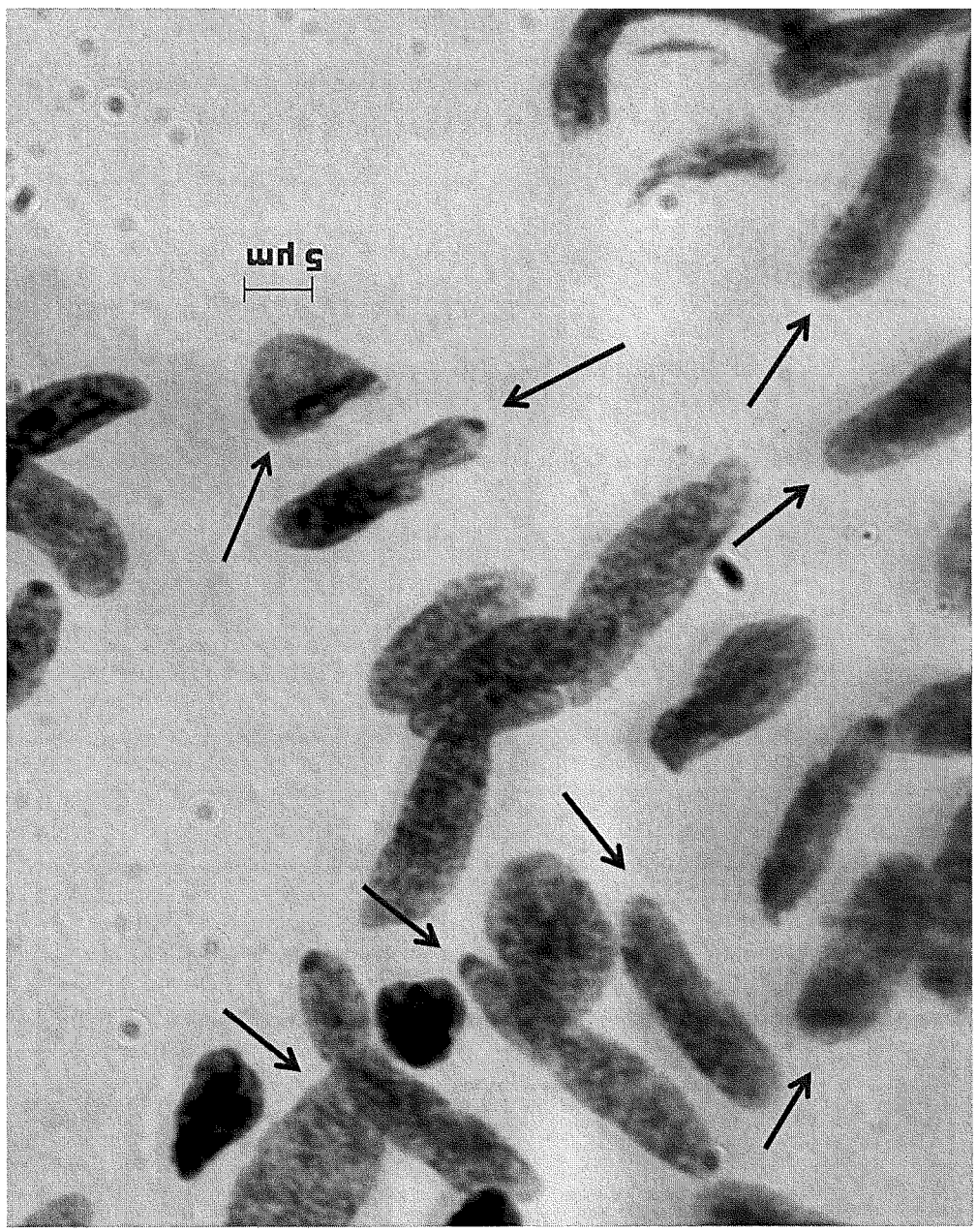
FIG. 31 is a ×100 microphotograph of metakaryotic stem cell (red arrow) and spindle-shaped nuclei of smooth muscle cells (blue arrows) in blood vessel of normal bladder, 4-year old child. Feulgen DNA stain (purple).
Figure 32:
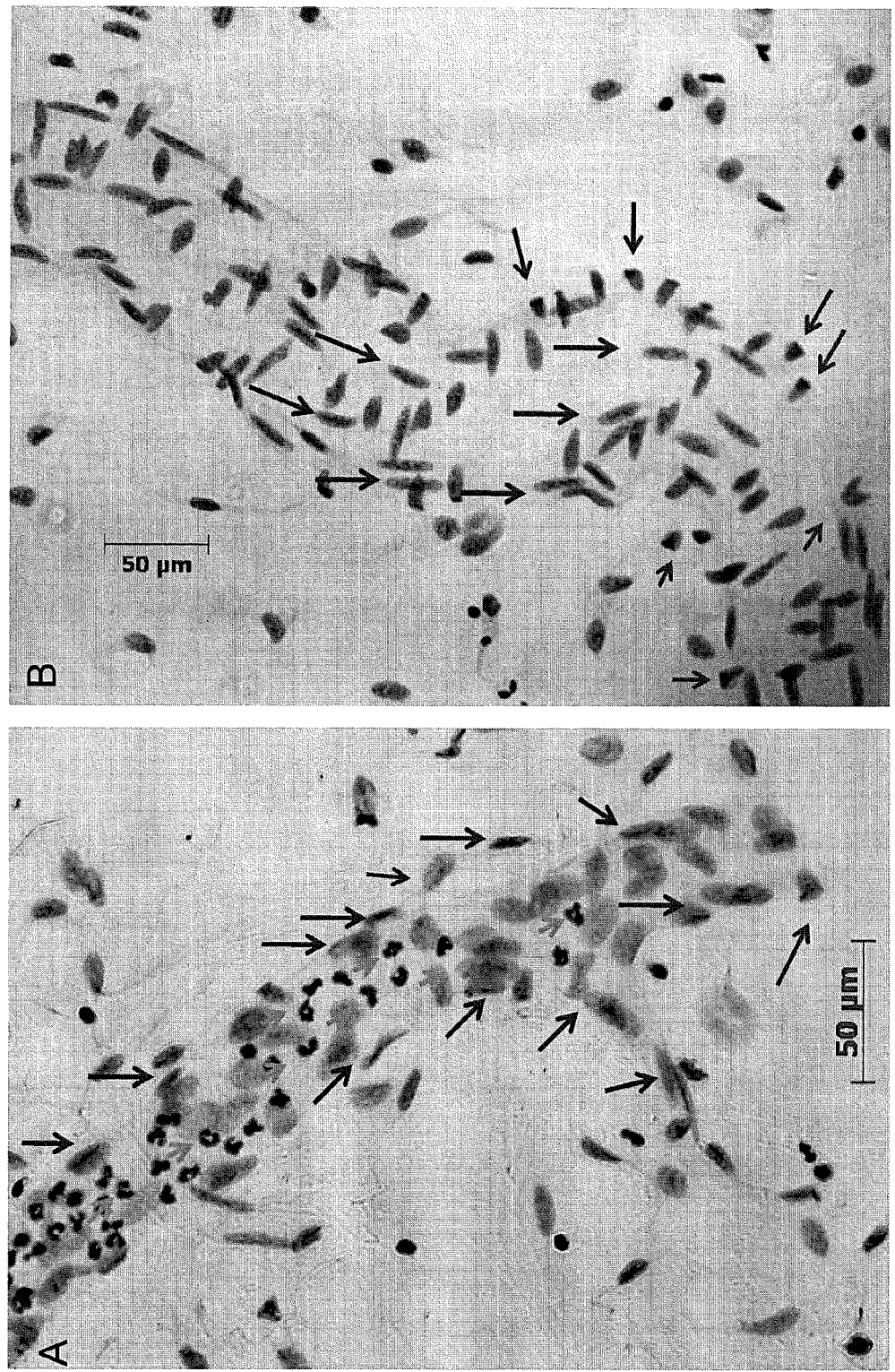
FIG. 32 B shows smooth muscle cells lining of a normal bladder, 4 years old child: Metakaryotic stem cells with bell-shaped nuclei (red arrows), smooth muscle cells with irregular nuclei (blue arrows). Feulgen DNA staining (purple).
Figure 33:
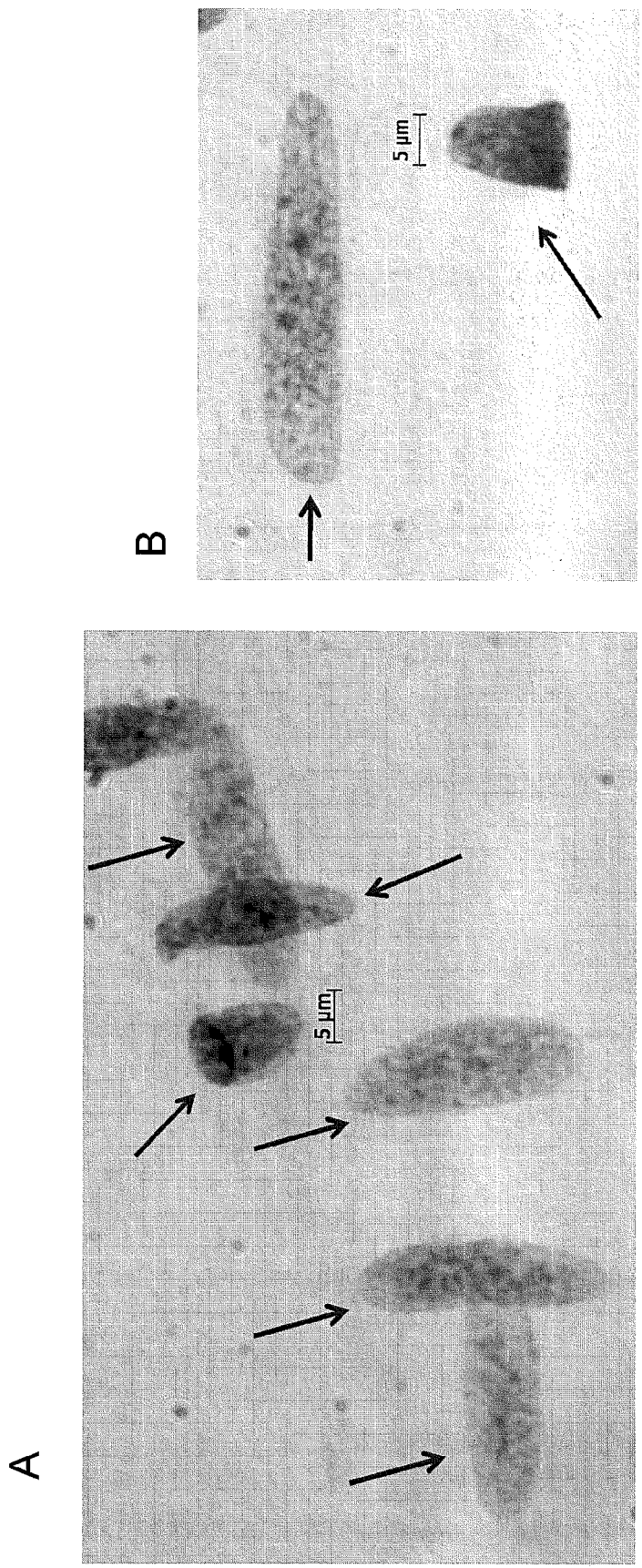
FIGS. 33A-B provide a pair of ×100 images of metakaryotic stem cells with bell-shaped nuclei (red arrows) and elongated irregular nuclei of smooth muscle cells (blue arrows) in blood vessels of bladder polyp, 3-year old male.

The invention provides both in vitro and in vivo methods of screening for agents to treat wound healing disorders, such as blood vessel wound healing disorders. In both the in vitro and in vivo methods, a candidate agent is evaluated for its ability to modulate either the number of metakaryotic cells, the number of proliferating (by symmetrical or asymmetrical amitosis) metakaryotic cells, or the migration of metakaryotic cells—relative to suitable controls, e.g., cultured cells or a mammal not treated with the candidate agent. The candidate agent can comprise any chemical entity, including a small molecule pharmaceuticals or biologic, such as a protein (e.g., growth factor, antibody, or aptamer), nucleic acid (including antisense molecules and aptamers), lipid, carbohydrate, or combinations thereof. The agent will typically be administered at dose or a range of doses, e.g., 2, 3, 4, 5, 6, or more doses, so as to elicit an effect on the number and/or distribution and/or migration of metakaryotic cells, particularly proliferating metakaryotic cells, in the culture or mammal In vitro screening methods comprise contacting cultured cells comprising proliferating metakaryotic cells and muscle cells with a candidate agent. In more particular embodiments, the cells are obtained from a mammal, such as a primate, a rodent, a canine, a feline, a porcine, an ovine, a bovine, or a leporine. In still more particular embodiments, the cells are obtained from a human. In certain embodiments, the cultured cells are obtained from umbilical cord, adventitia, mesenchymal tissue, or aortic arch. In particular embodiments, the cultured cells are HT29 human colon adenocarcinoma cells, as described in Example 6 of U.S. Patent Application Publication No. 2010/0075366 A1, including FIGS. 28-30, and their descriptions, all of which are incorporated by reference. In particular embodiments, the cultured cells comprising proliferating metakaryotic cells and muscle cells are primary cells. In more particular embodiments, the primary cells are obtained from umbilical cord, vascular adventitia, or aortic arch.

In vivo screening methods comprise administering a candidate agent to a mammal. In more particular embodiments, the mammal is a non-human mammal. In still more particular embodiments, the mammal is a non-human primate, a rodent, a canine, a feline, a porcine, an ovine, a bovine, or a leporine. In yet still more particular embodiments the mammal is a rodent, such as a mouse, rat or guinea pig. In still more particular embodiments, the mammal is a guinea pig. In some embodiments, the mammal is predisposed (e.g., genetically or via diet or drug treatment) to develop a wound healing disorder. In certain embodiments, the wound healing disorder arises from a surgical intervention, e.g., surgical insult such as transplantation, angioplasty, stenting, or direct intentional tissue damage, e.g., by chemical fixation, radiation, excess heat or cold, infarct, stabbing, cutting, or blunt trauma. In more particular embodiments, the mammal is both predisposed to develop a wound healing disorder and exposed to a surgical intervention. In certain embodiments the wound healing disorder is a blood vessel wound healing disorder. In more particular embodiments, the blood vessel wound healing disorder is restenosis.

In certain embodiments, the in vitro or in vivo screening methods of the invention may further comprise the step of detecting particular non-metakaryotic cells, such as the irregular nuclei characteristic of smooth muscle cells, e.g., the methods my comprise a step of detecting smooth muscle cells, and in more particular embodiments, change in the number of smooth muscle cells, i.e. an increase or decrease in the number of these cells.

Treatment Methods

The screening methods described above provide agents that can be used to treat wound healing disorders. Therefore, the invention also provides methods of treating a subject having a wound healing disorder. For example, a subject with any wound healing disorder as herein described can be administered an effective amount of (and for a sufficient period of time) an agent that modulates, e.g., the number of metakaryotic stem cells, the number of proliferating metakaryotic stem cells, or the migration of metakaryotic stem cells. For example, in wound healing disorders characterized by aberrant excessive tissue generation, the subject is administered an agent that decreases the number of metakaryotic stem cells, the number of proliferating metakaryotic stem cells, or the migration of metakaryotic stem cells. Conversely, in wound healing disorders characterized by aberrant inadequate tissue generation, the subject is administered an effective amount of an agent that increases the number of metakaryotic stem cells, the number of proliferating metakaryotic stem cells, or the migration of metakaryotic stem cells.

Agents that can be used in the therapeutic methods provided by the invention include any of those identified by the methods provided by the invention. Other agents that can or are suspected of being able to inhibit: the number of metakaryotic stem cells, the number of proliferating metakaryotic stem cells, or the migration of metakaryotic stem cells, are disclosed in, for example, U.S. Patent Application Publication No. 2009/0304662 and International Application No. WO2008/156629, the entire teachings of which are incorporated by reference in their entirety. The agent administered to a subject agent can comprise any chemical entity, including a small molecule pharmaceuticals or biologic, such as a protein (e.g., growth factor, antibody, or aptamer), nucleic acid (including antisense molecules and aptamers), lipid, carbohydrate, or combinations thereof. In particular embodiments, the invention provides a method of treating a subject with a wound healing disorder characterized by aberrant inadequate tissue generation by administering isolated metakaryotic stem cells.

Also encompassed by the present invention are methods of treating a wound healing disorder characterized by inadequate tissue generation in a subject in need thereof by culturing, or isolating, wound healing metakaryotic stem cells and administering them to the subject, directly, or indirectly in an effective amount to stimulate/activate tissue generation. For example, metakaryotic cells can be cultured into cohesive sheets of cells and contacted with an area of the subject needing tissue generation.

The skilled artisan will understand that the source of cells for these methods (such as a cell culture or tissue sample) should comprise metakaryotic stem cells. The methods may, in some embodiments, further include one or more steps of isolating and/or expanding the metakaryotic stem cells, e.g., by culturing, by means described herein and readily understood and implemented by the skilled artisan without undue experimentation.

A description of example embodiments of the invention follows.

EXEMPLIFICATION

The following exemplifications support the present invention, which is directed to diagnostic, therapeutic, and screening methods for wound healing disorders, such as blood vessel wound healing disorders. Exemplary blood vessel wound healing disorders include injury-induced neointimal hyperplasia and restenosis. In more particular embodiments, the blood vessel wall disorder is restenosis.

Materials and Methods

The procedures used fixed and stained mammalian tissue sections some 3-5 mm in thickness in which cellular adhesions were chemically or enzymatically disrupted (dissociated or macerated) to a degree that permits an orderly spreading of the tissue on a microscope slide [Gostjeva et al. 2009]. Small morphological structures such as stained nuclei and larger structures such as colonic crypts and blood vessels were observed, with some distortion inherent in tissue spreading.

Surgical tissue discards were provided within a half hour of resection, preferably within fifteen minutes [Gostjeva et al., 2006]. Sheets (up to 1 cm$^2$) of stripped epithelial layers of tissues, 3-5 mm of restenotic plaque tissues and adjacent normal mesenchymal areas were placed immediately into freshly prepared 4° C. Carnoy's fixative (3:1, ethanol:glacial acetic acid) upon dissection. The volume of fixative was at least three times the volume of the tissue sample. Fresh fixative was replaced three times every 45 minutes for a total of three hours of fixation. Carnoy's fixative was then replaced by 4° C. 70% ethanol Samples could then be stored up to a year at 4° C. to −20° C.

About 1 mm$^2$ pieces were excised from the whole fixed tissue sample for spreading and DNA staining. Each piece was rinsed in distilled water and placed in a test tube with 2 ml of collagenase in distilled water solution pre-warmed to 37° C. (water was added to collagenase powder at room temperature). Tubes were placed in a 37° C. shaker water bath for about 10 minutes (Collagenase Type II, 100 mg, Calbochem Inc., 273 U/mg). Duration of collagenase tissue dissociation was as follows: 3 hours for epithelial tissues, 4 hours for plaque tissues, up to 6 hours for normal smooth muscle tissues of arteries or cardiac muscle tissues. The collagenase digested ~1 mm cut tissue sections were then rinsed in water and placed for 15 minutes in 45% acetic acid in a 2 ml tube. The tissue spreading procedure was conducted in a drop of 45% acetic acid on microscopic slide. Each ~1 mm$^2$ enzymatically digested section was bisected to form two ~0.5×1 mm pieces of fixed, macerated tissue. Each piece was transferred into ~5 µL of acetic acid on a clean microscope slide and covered with a 22×22 mm cover slip. Holding the cover slip by the edges slight pressure was applied on the tissue sample to locate it in the middle of the slide.

The quality of the spreading was checked using a 20× phase-contrast objective for each individual sample. An indication of a good tissue spread was that there were no damaged nuclei on the edges of the whole tissue spread while 3D tissue structures (blood vessels, crypts) were pressed into what is essentially a monolayer preserving the morphological integrity. Each well-spread sample slide was placed immediately on a dry ice surface. After 2 minutes when the spread tissue sample was completely frozen a razor blade is inserted under one edge of the cover slip and it was gently lifted off. Slides were allowed to dry in a dust free environment for not less then one hour.

To stain nuclei by a Schiff's reagent as used herein using Feulgen's reagent it was necessary to perform hot acid hydrolysis of tissue spread on microscopic slides. Slides were placed in a Coplin jar, covered with pre-warmed (60° C.) 1 N hydrochloric acid solution for 8 minutes, then quickly rinsed in distilled water. Water drops were shaken off and slides were dried for 3 hours in a dust free environment. Slides were then ready for Feulgen staining.

Staining procedures were performed at room temperature. Slides were placed in Coplin jars and filled with Schiff's reagent (Art. 9033, Merck) to react with the partially depurinated DNA of the nuclei. Slides were immersed in staining solution for one hour, rinsed in the same Coplin jar two times in 2×SSC (trisodium citrate 8.8 g/L, sodium chloride 17.5 g/L), once for 30 sec and once quickly. Slides were then rinsed with distilled water. The slides at this stage were suitable for observation of the distribution of DNA in nuclei including, for example, measurement of Feulgen DNA amounts in nuclei or condensed chromosomes of mitotic, eukaryotic cells by quantitative image analysis (Greilhuber and Temsch, Genome 44:826-30 (2001); Hardie, Gregory and Hebert, *J. Histochem Cytochem* 50:735-49 (2002)).

To achieve superior resolution and imaging of interphase nuclei, some slides were further stained with Giemsa. Immediately after rinsing in 2×SSC slides were placed in 1% Giemsa solution (Giemsa, Art. 9204, Merck) for 5 minutes then rinsed quickly first in Sörenssen buffer (disodium hydrogen phosphate dihydrate 11.87 g/L, potassium dihydrogen phosphate 9.07 g/L) and then distilled water. Water drops were shaken off the slide as if one were shaking an old-fashioned thermometer to avoid erosion of the stain. The slides were placed in a dust free environment to dry at room temperature for one hour. They were then placed in a Coplin jar filled with Xylene for at least 3 hours to remove fat. Cover slips were glued to the slides with DePex mounting media and permitted to dry for 3 hours at which time they were ready for high resolution scanning Example 1

Visualization of Metakaryotic Cells in Fetal Kidney Artery

Figure 3:
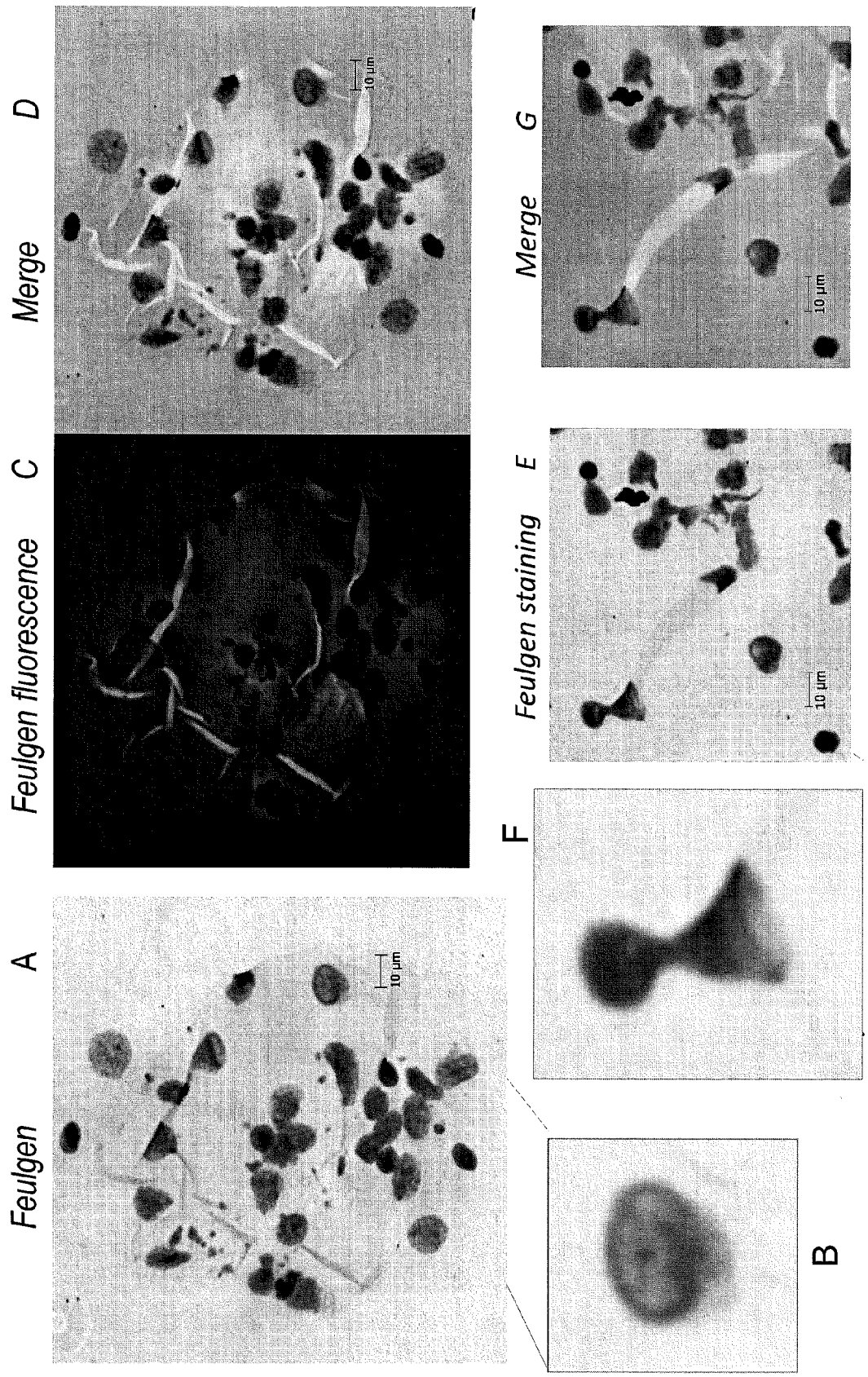
FIGS. 3A-G are micrographs showing non-syncytial bell-shaped nuclei (arrows) human fetal kidney artery, 9 wks. New cell forms including cells with irregular nuclei found in smooth muscle cells are seen to arise from metakaryotic cells with asymmetrical amitoses.
Figure 4:
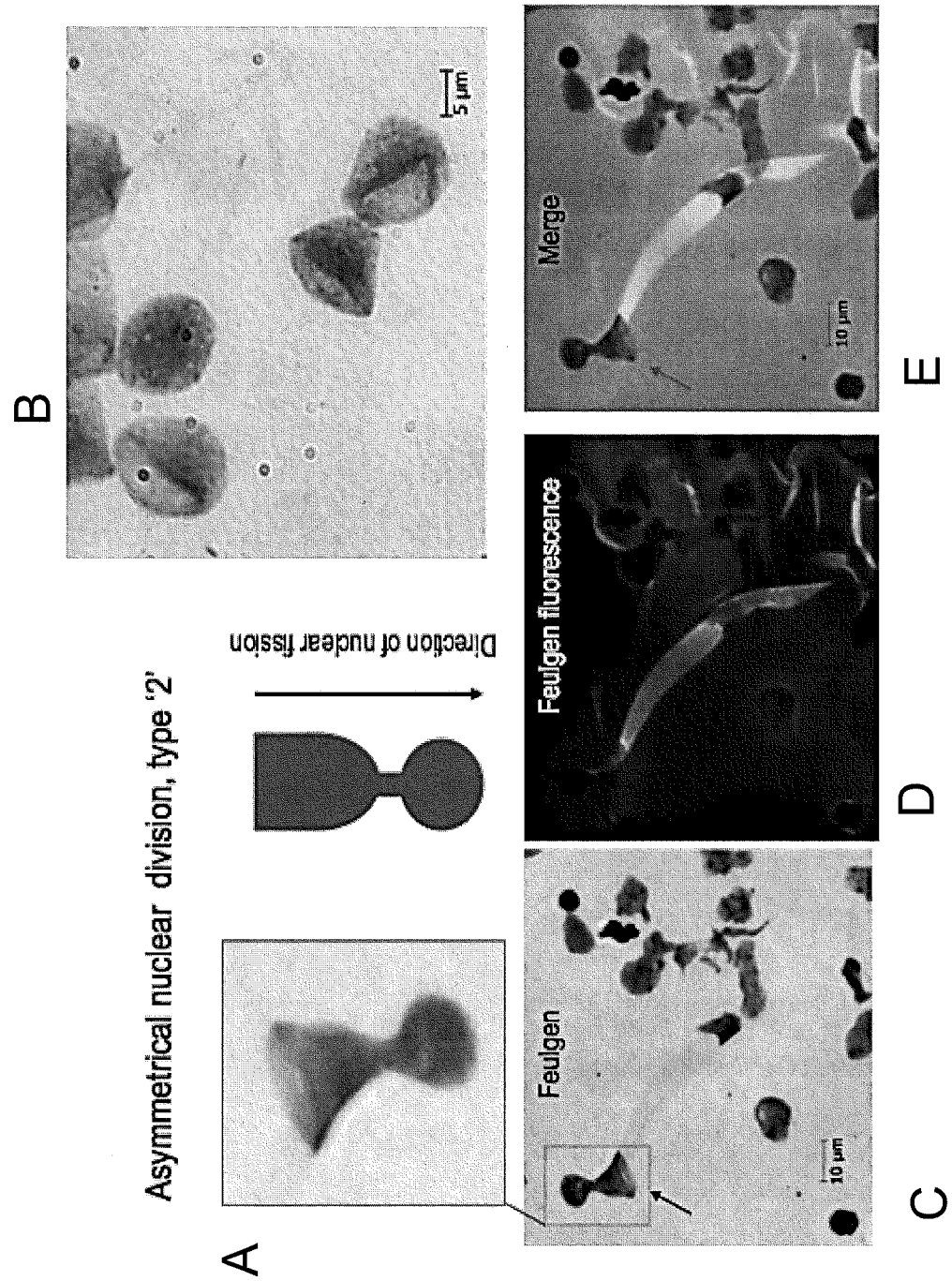
FIGS. 4A-E are micrographs of human fetal kidney artery, 9 wks
Figure 5:
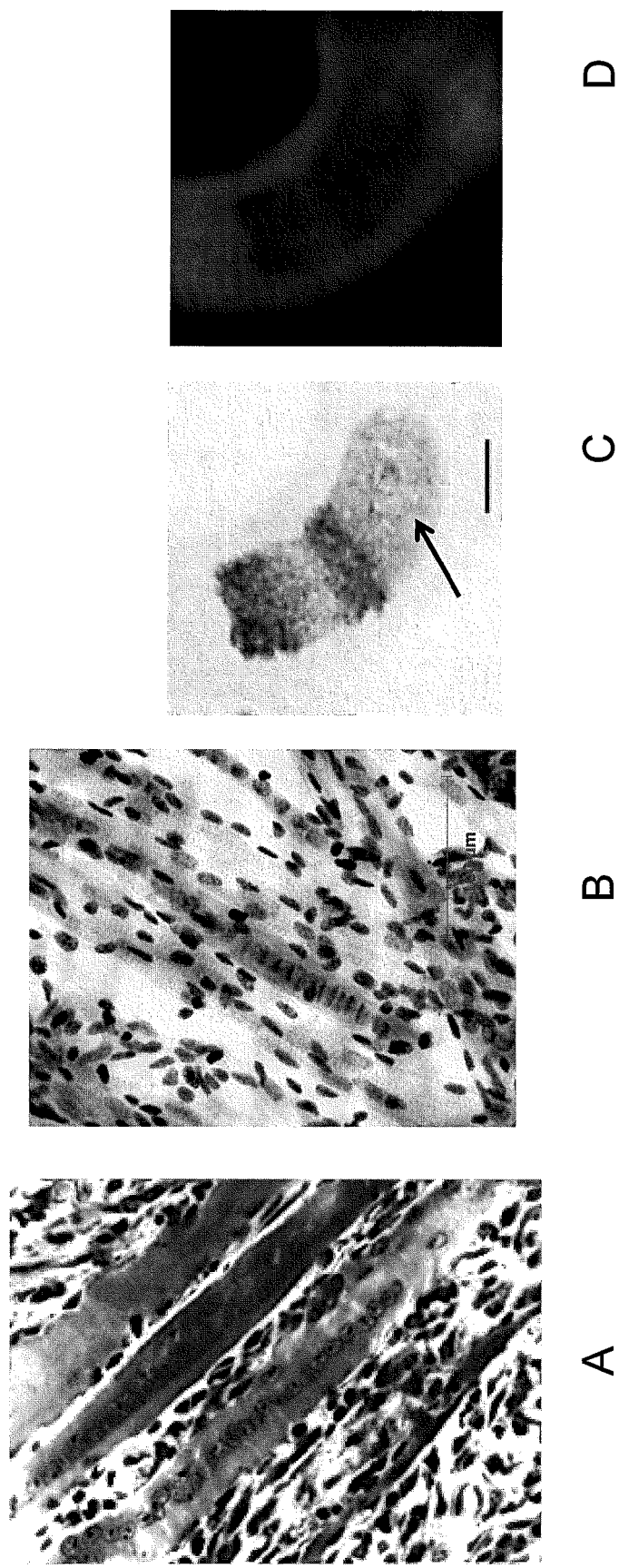
FIGS. 5A-D are micrographs showing the appearance of fetal-like tubular syncytial (myotubes) in wound healing.

The tissues shown in FIGS. 2-4 were prepared for visualization of the metakaryotic stem cells substantially as described above. The tissues were obtained from human fetal kidney artery.

Example 2

Figure 6:
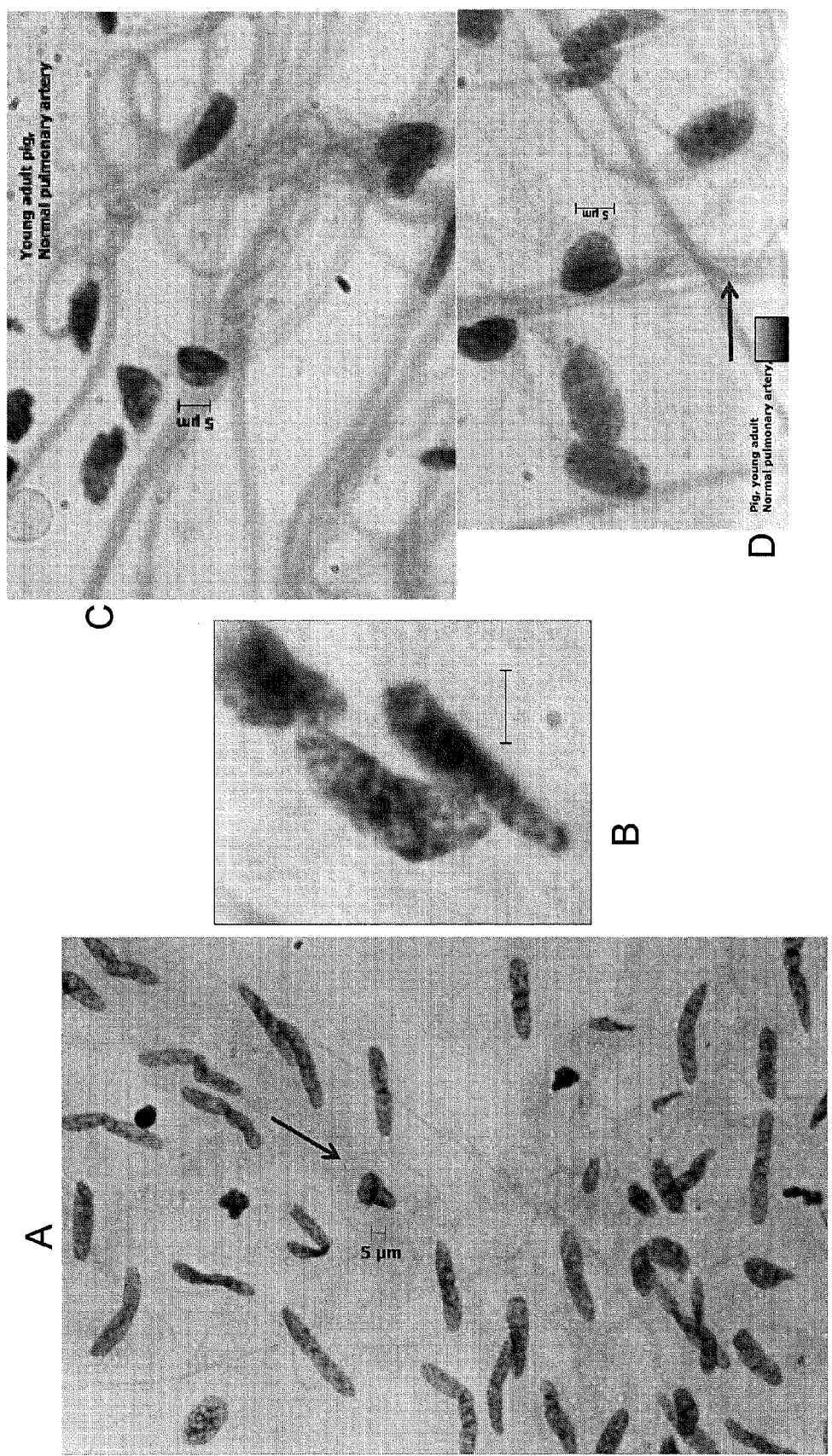
FIGS. 6A-D are micrographs showing the following.
Figure 8:
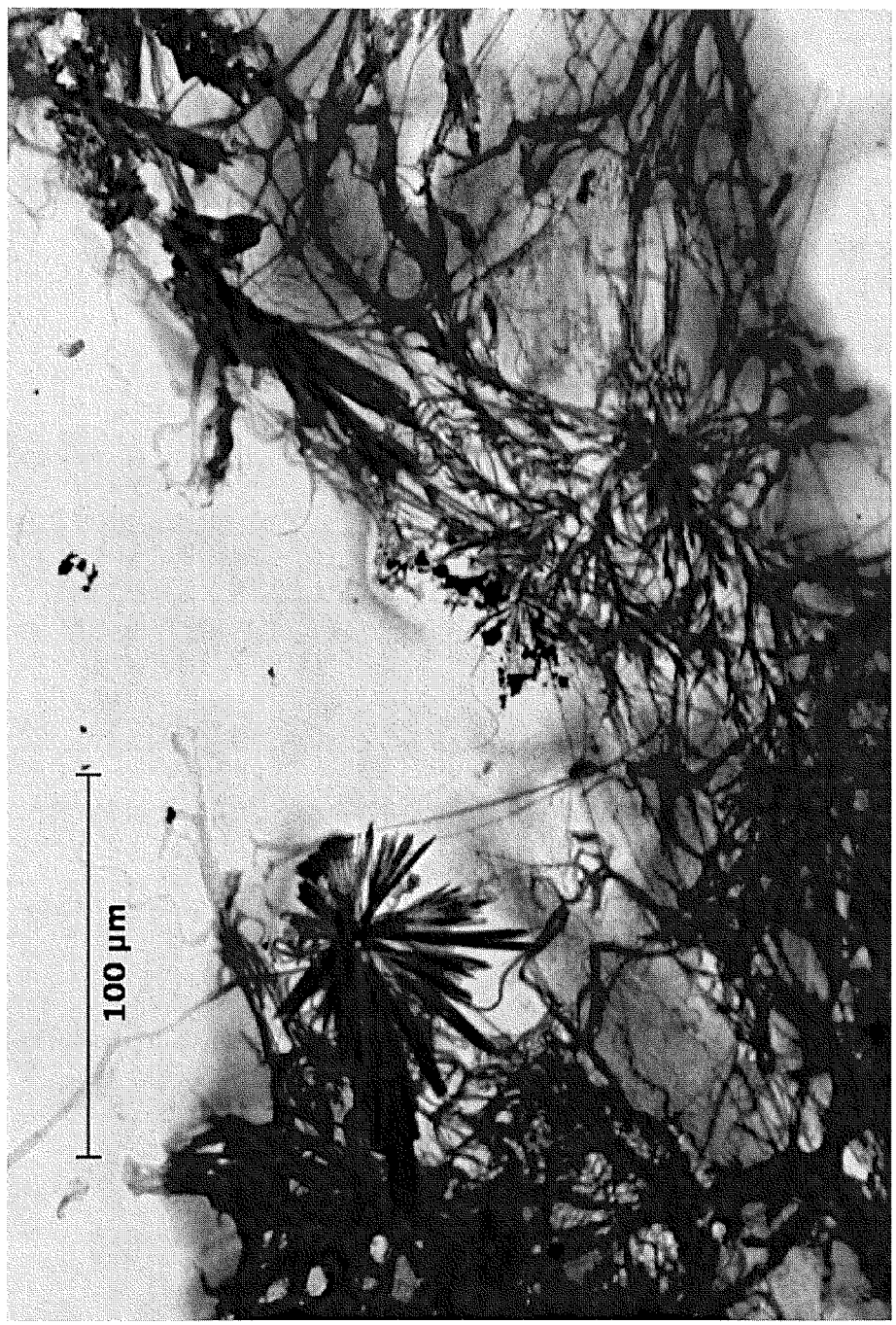
FIG. 8 is a micrograph of a biopsy from a pediatric patient suffering from post-transplant restenosis after heart transplant. The bright magenta spicules are calcified structures on fibronectin fibers distributed along the vessel walls that constitute "hardening of the arteries" also known in this case of rapid restenosis as "galloping atherosclerosis."
Figure 11:
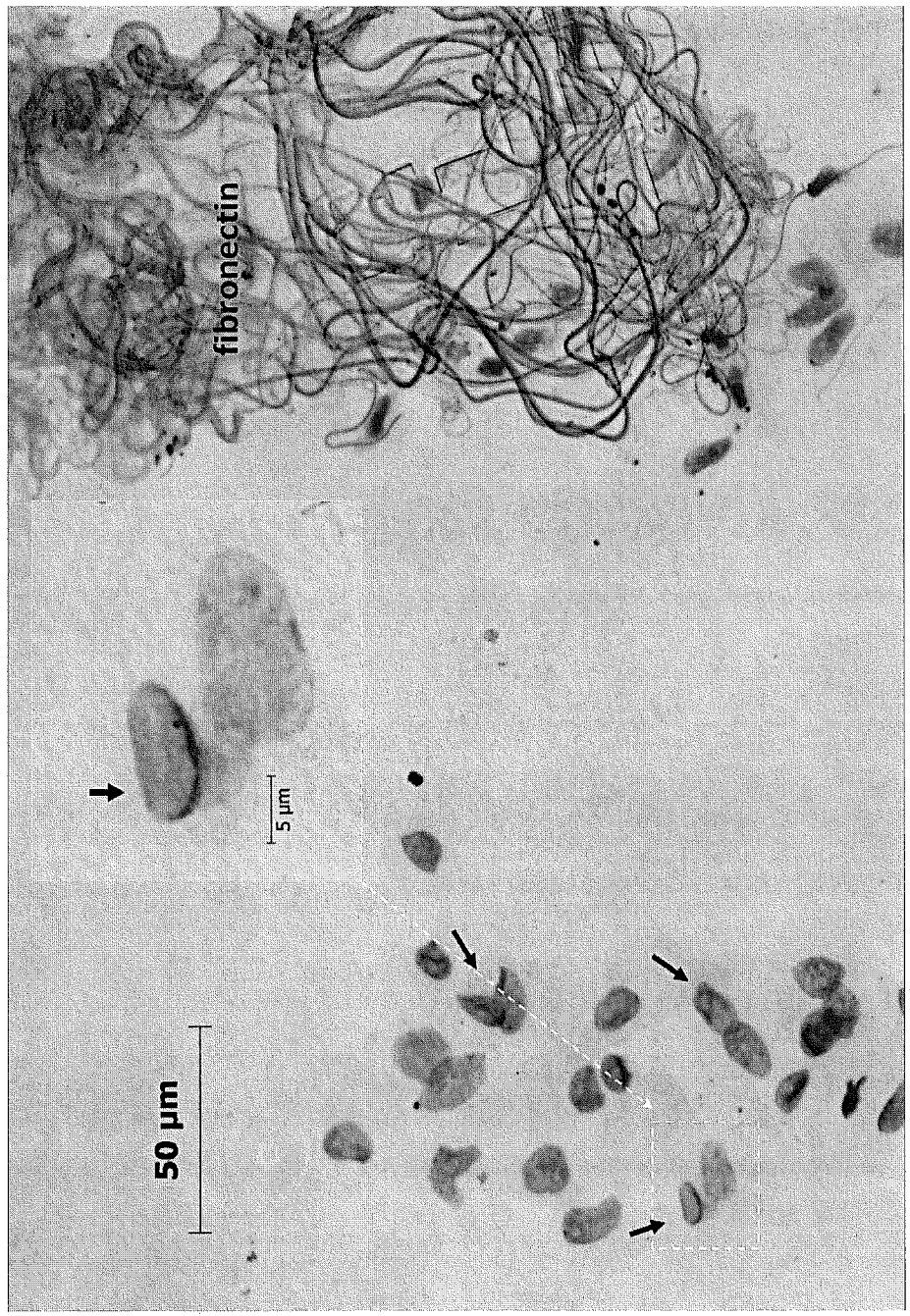
FIG. 11 shows a micrograph of a biopsy from a patient suffering from post-transplant restenosis. A mass of fibronectin is seen on the right with associated cells with bell and other shaped nuclei. On the left various bell shaped nuclei are seen giving rise to cells with other nuclear forms including those of smooth muscle cells, at higher resolution the blow up shows another example of asymmetrical amitosis as pictured in FIG. 4A.
Figure 12:
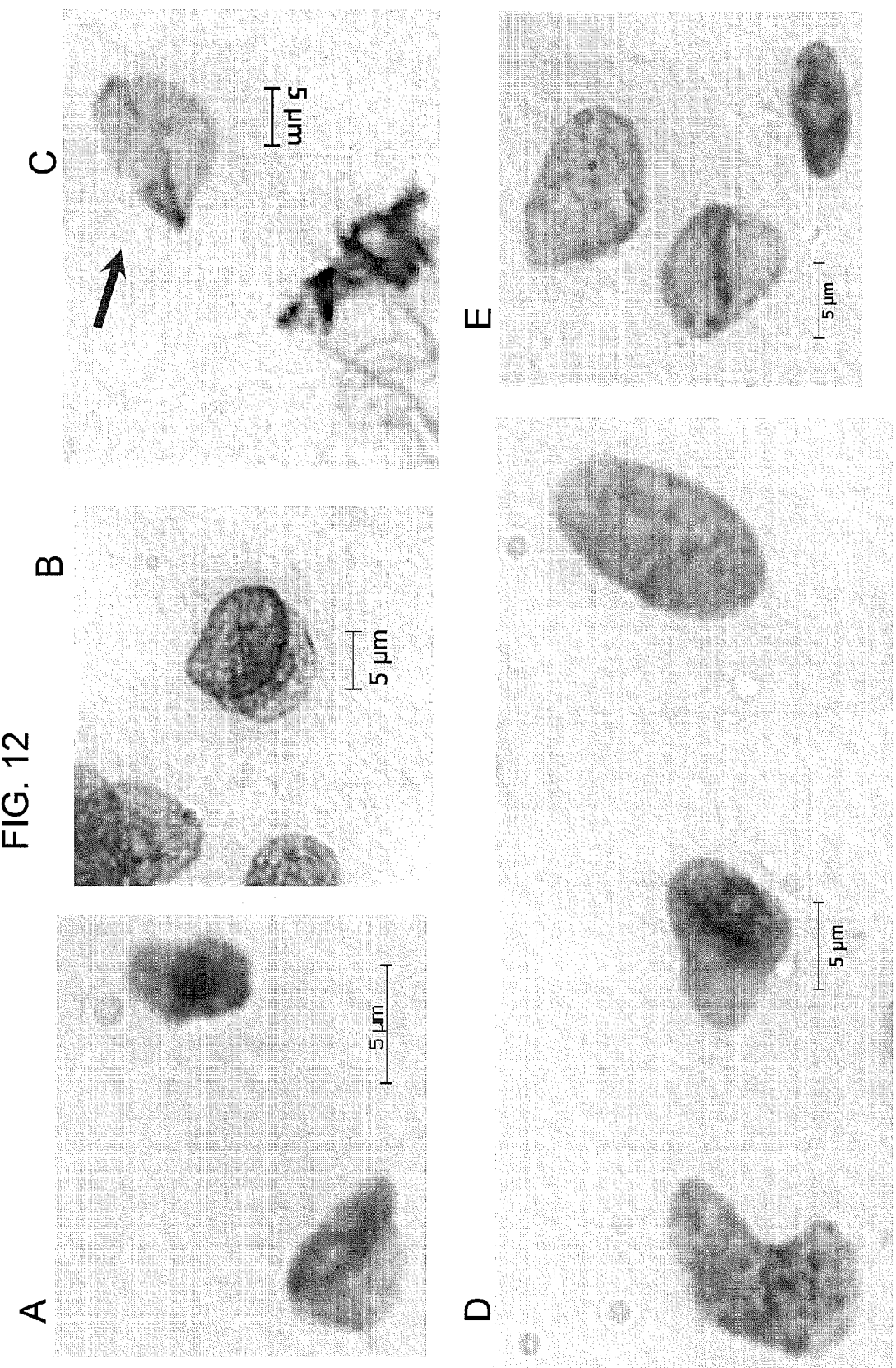
FIGS. 12A-E are micrographs showing bell-shaped nuclei (arrows) in a restenotic plaque in which the metakaryotic cell fraction was estimated to be ~$1\times10^{-3}$ (heart transplant, 2 year old child).
Figure 13:
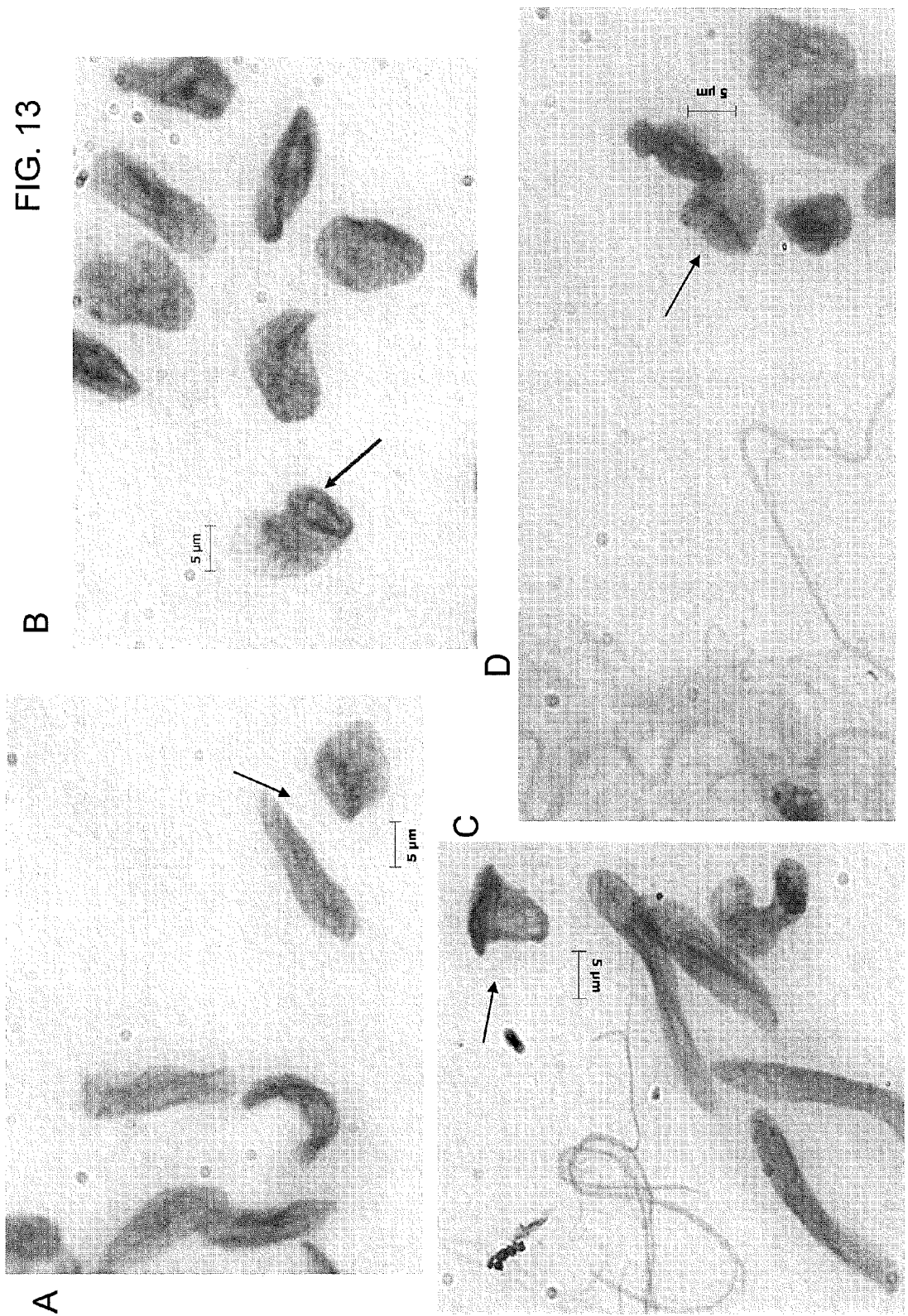
FIGS. 13A-D are a series of micrographs showing additional examples of bell-shaped nuclei generating smooth muscle cell nuclei as in FIG. 12.
Figure 14:
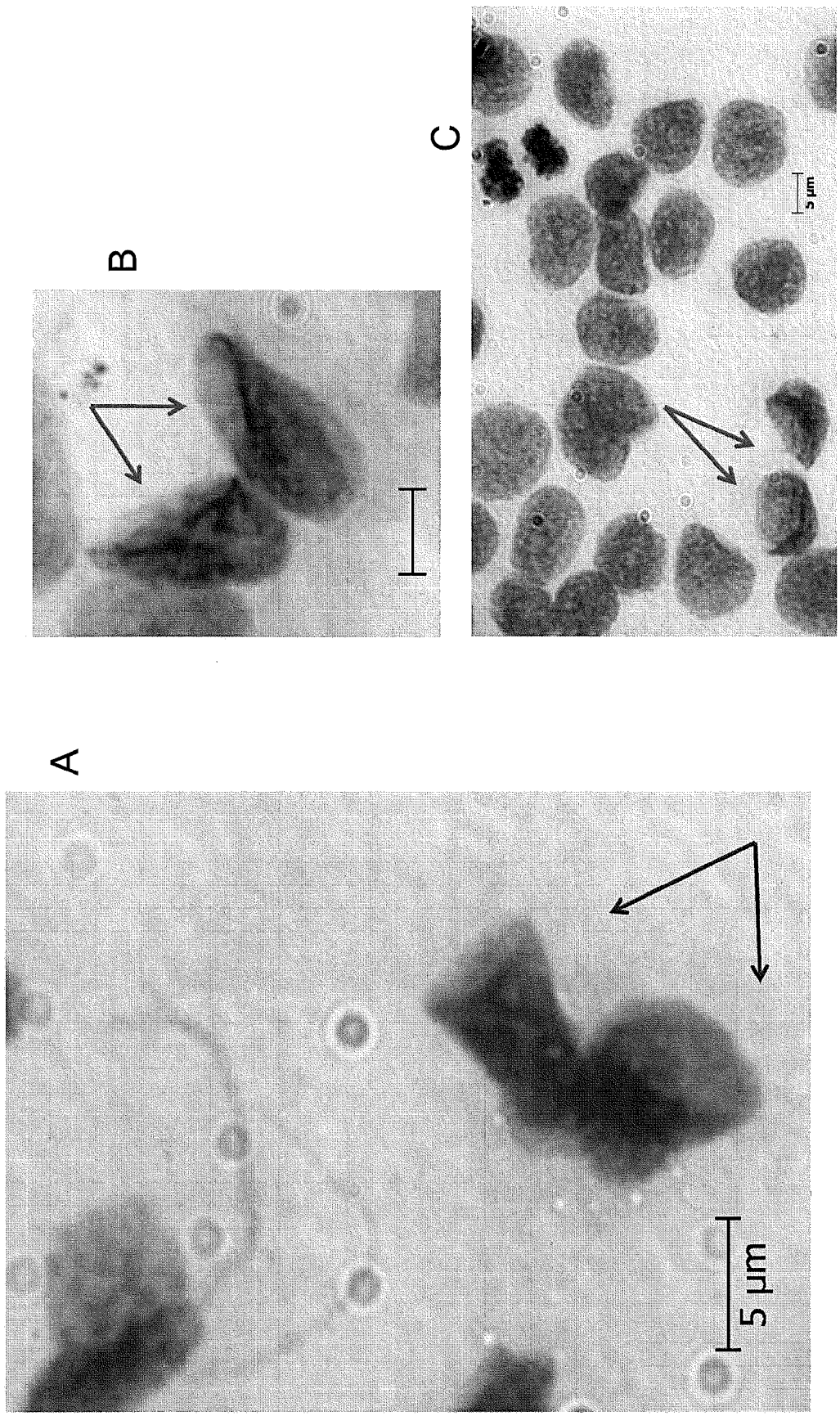
FIG. 14 is a series of micrographs of pairs of metakaryotic stem cell nuclei in restenotic plaque (heart transplant, 2 Yrs) (FIG. 14A), fetal gut (5-7 wks) (FIG. 14B), and HT 29 carcinoma cell line (FIG. 14C).
Figure 16:
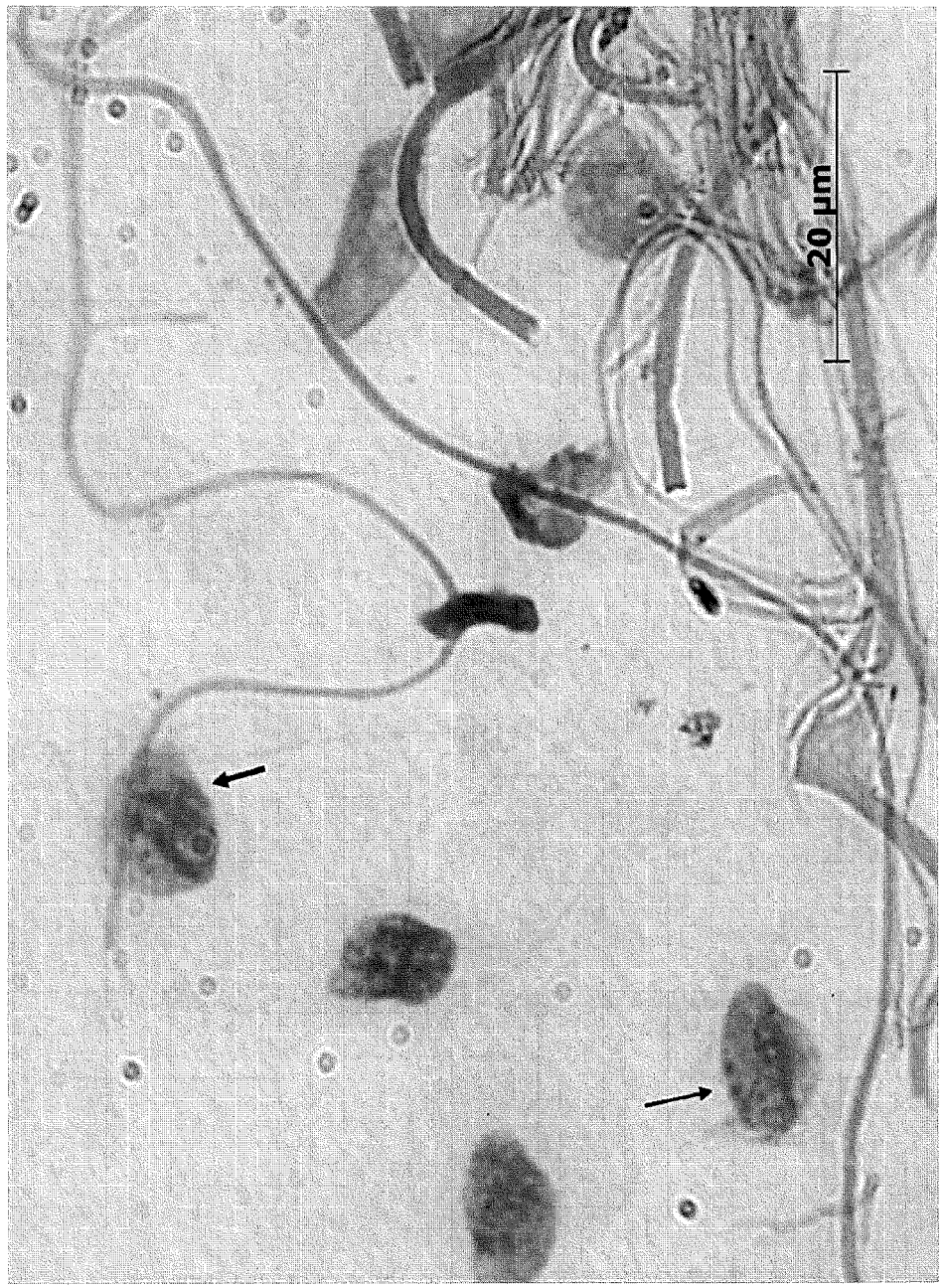
FIG. 16 shows a micrograph of a biopsy from a patient suffering from post-transplant restenosis. Two bell shaped metakaryotic stem cell nuclei (arrows) are seen in the vicinity of fibronectin fibers along with nuclei of smooth muscle cells and other nuclear indeterminant forms.
Figure 17:
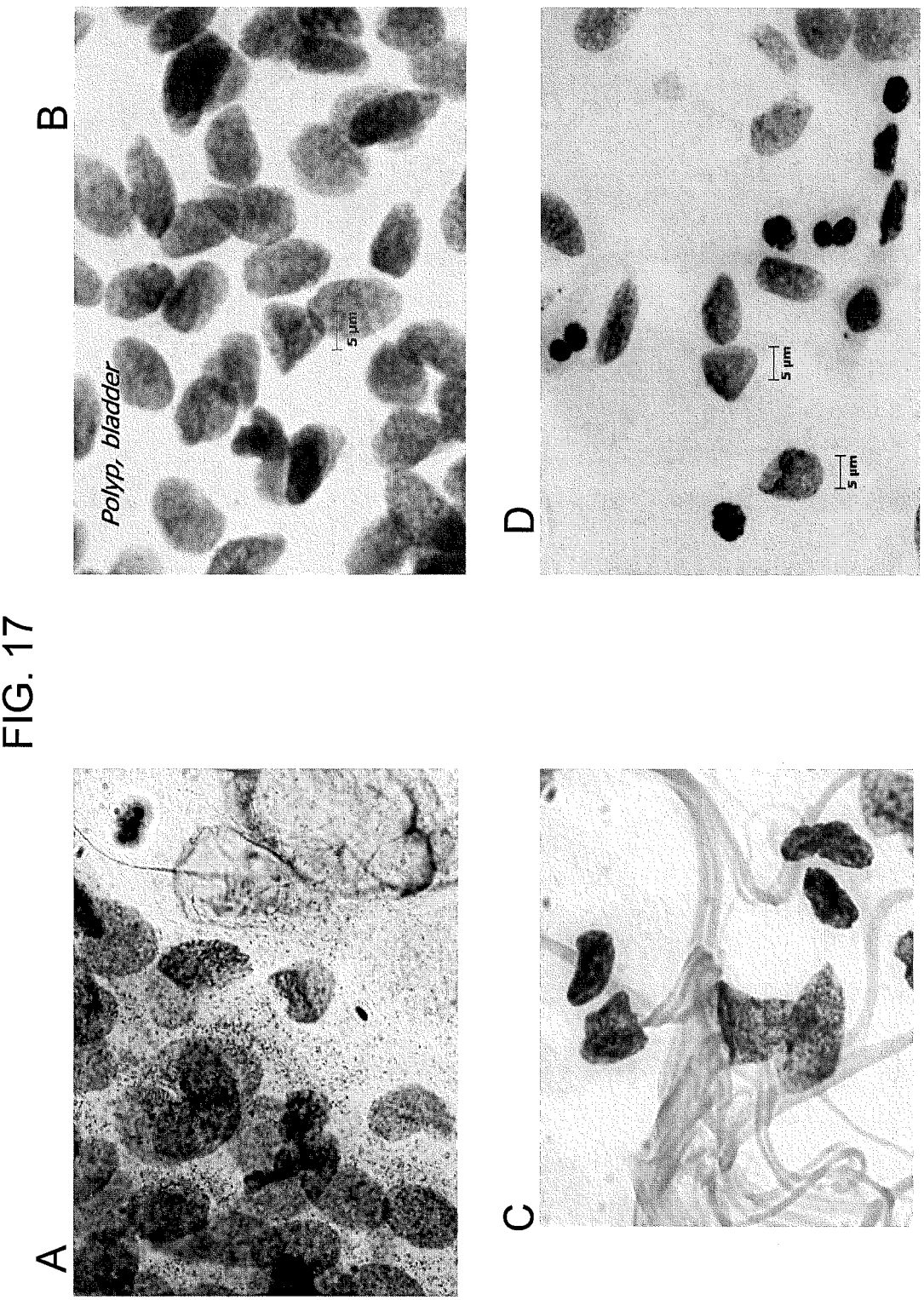
FIGS. 17A-D are micrographs showing neovasculogenesis and wound healing, in a patient who had sustained a bladder polyp catheter injury.
Figure 18:
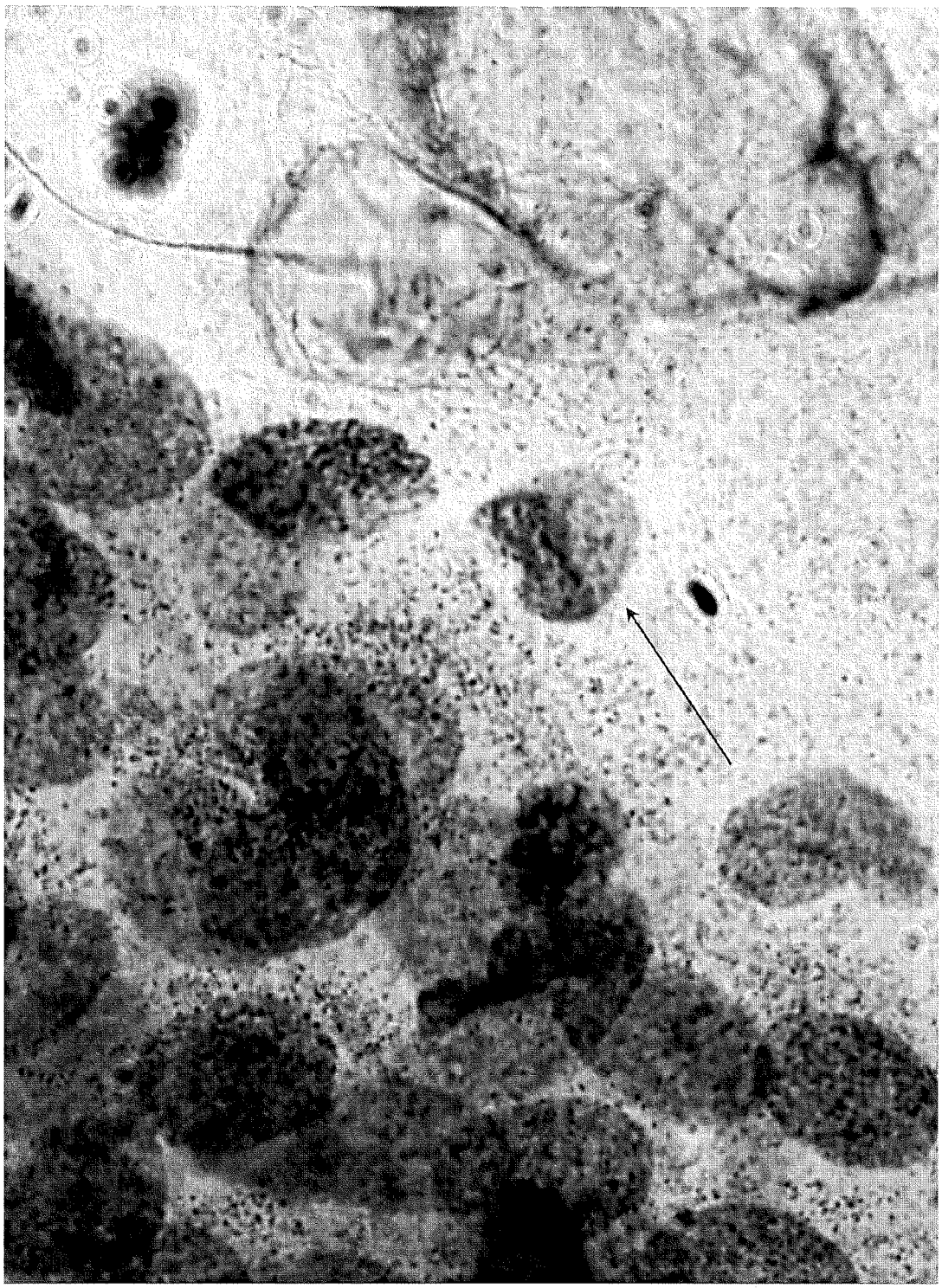
FIG. 18 is a micrograph of cells, including metakaryotic stem cells involved in would healing in the skin of a 6 month old human child.
Figure 19:
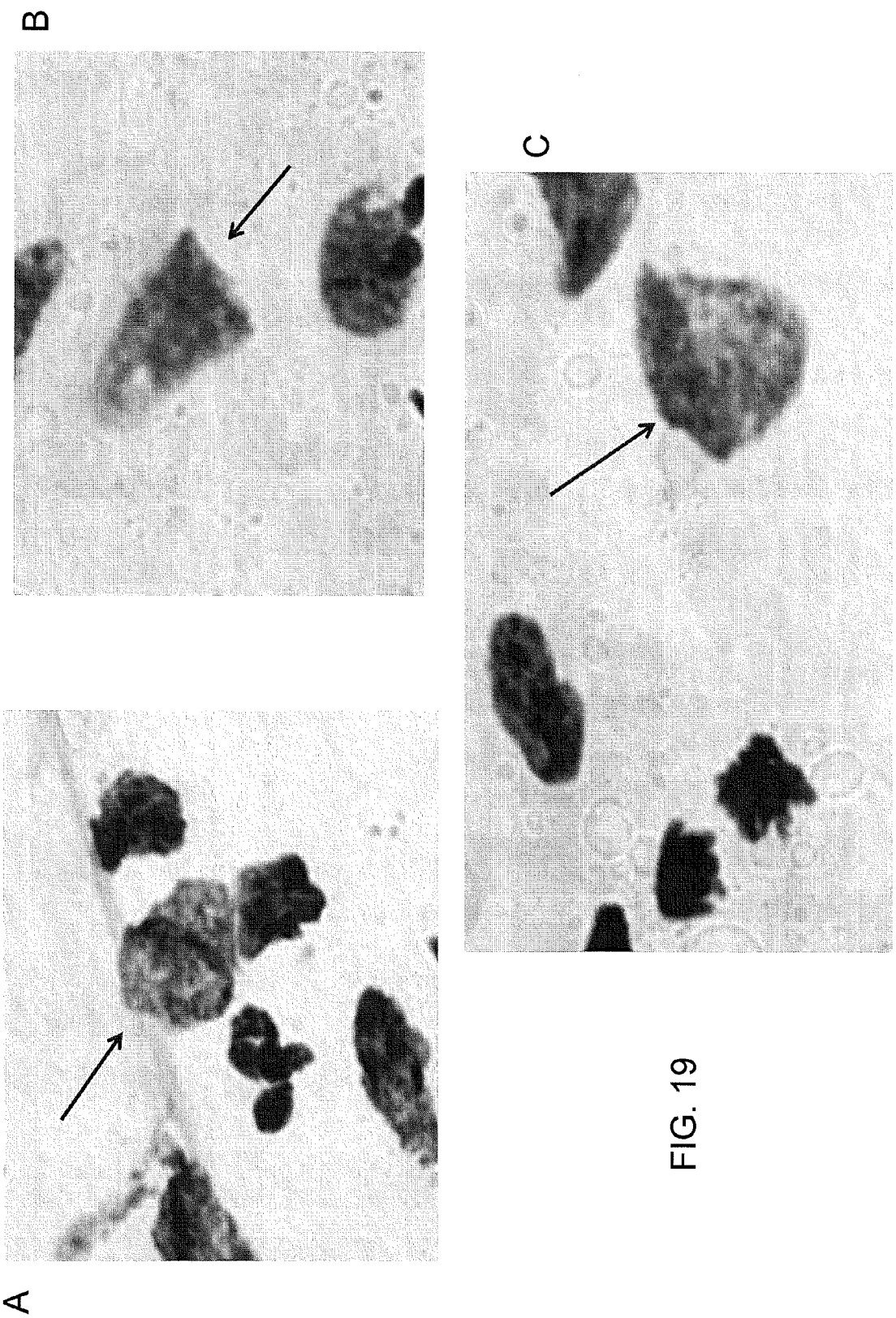
FIGS. 19A-C are micrographs of cells, including metakaryotic stem cells involved in would healing in the skin of a 6 month old human child.
Figure 20:
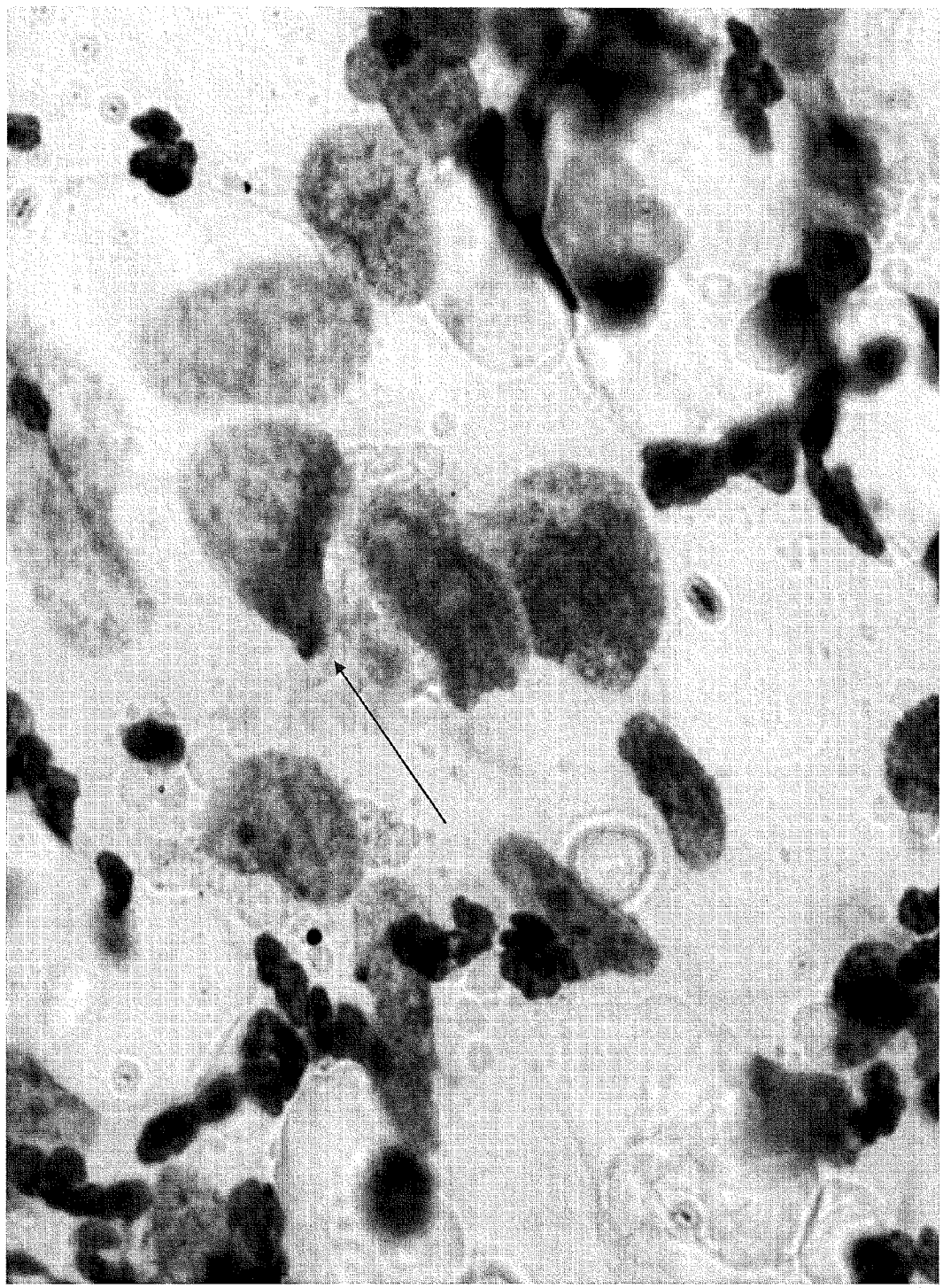
FIG. 20 is a micrograph of cells, including metakaryotic stem cells involved in would healing in the skin of a 6 month old human child.
Figure 21:
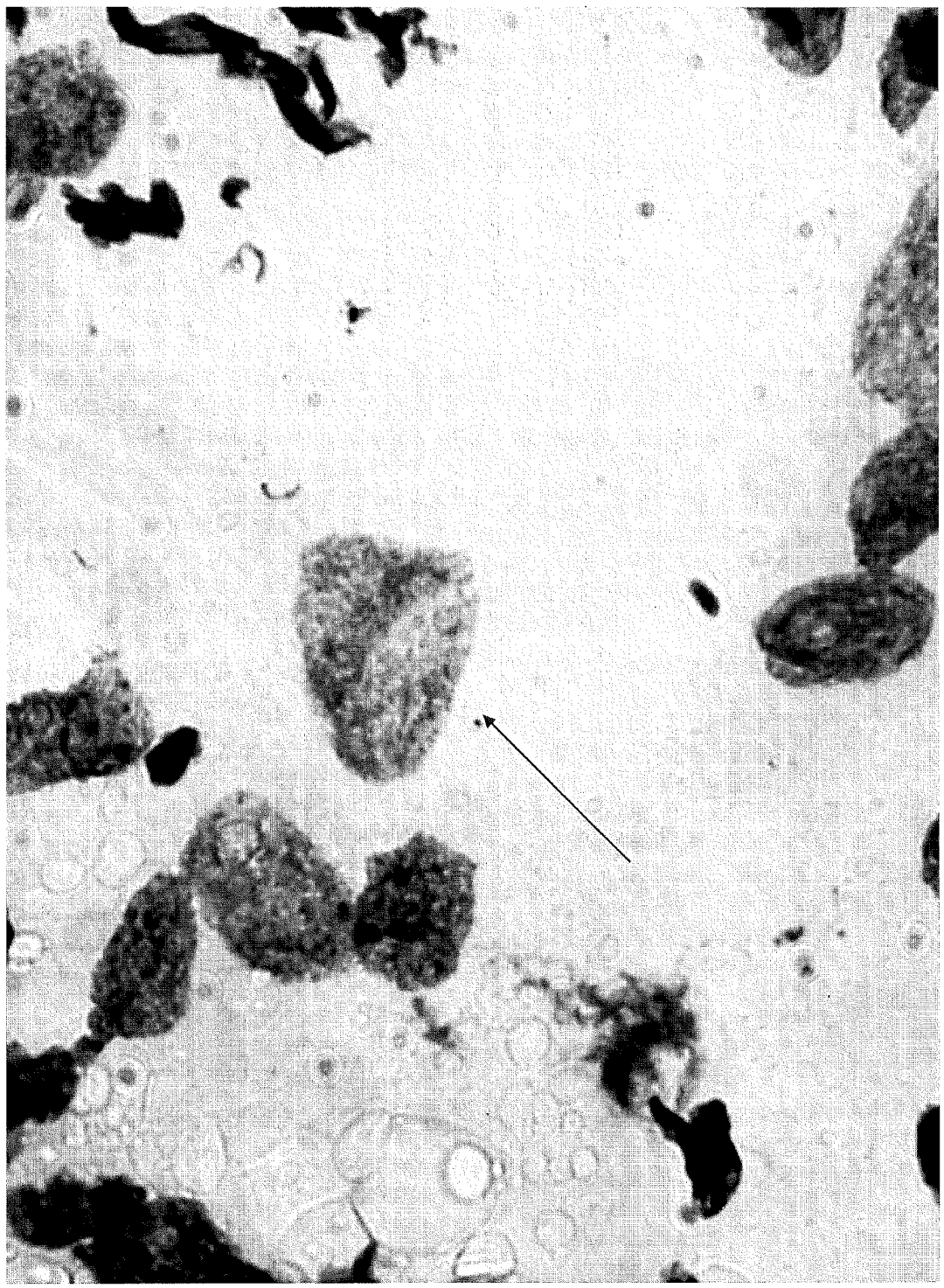
FIG. 21 is a micrograph of cells, including metakaryotic stem cells involved in would healing in the skin of a 6 month old human child.
Figure 23:
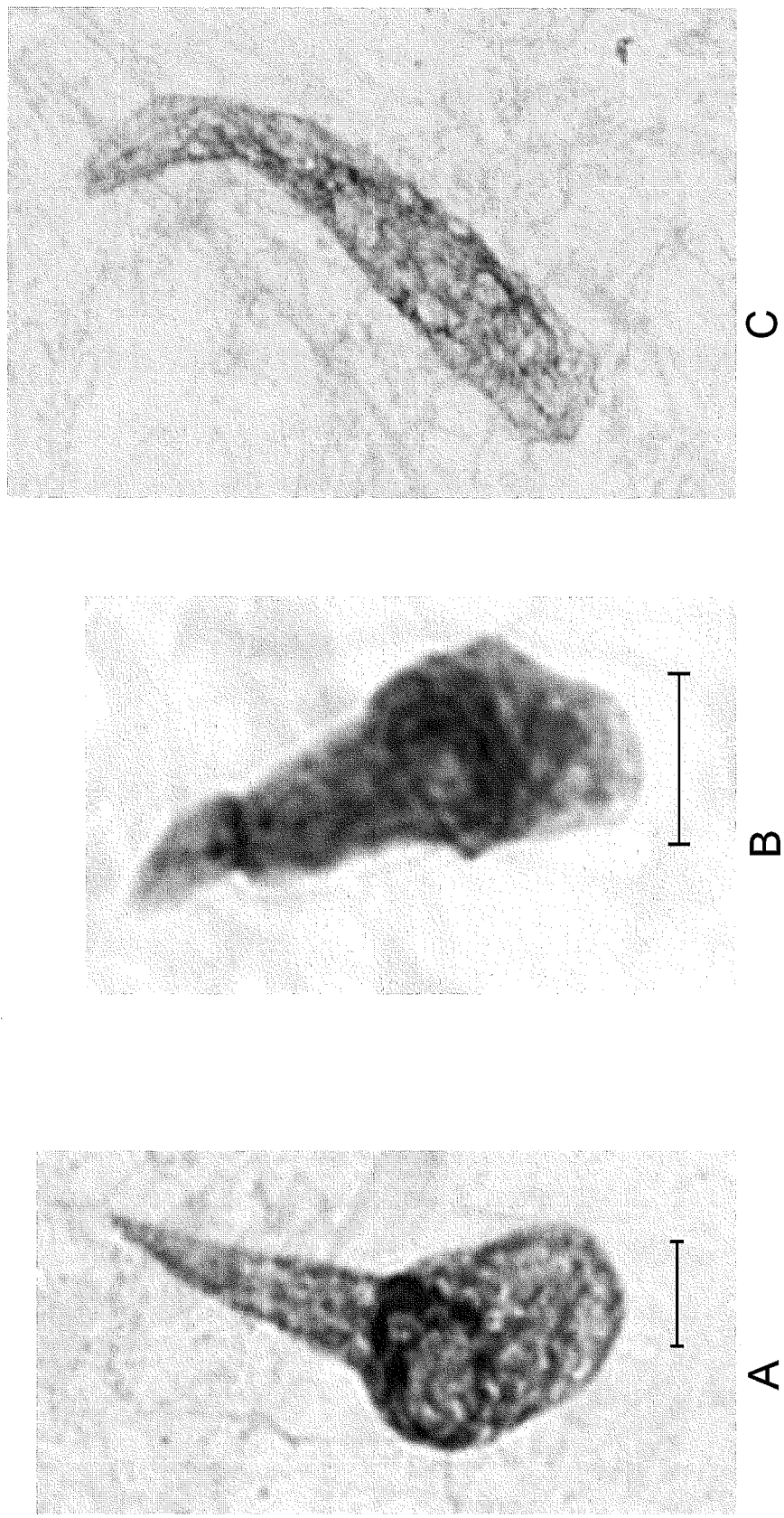
FIGS. 23A-C are micrographs of asymmetrical nuclear fissions in stenotic vein (non-mitotic origin of smooth muscle cells); Feulgen purple stain for nuclear DNA.
Figure 24:
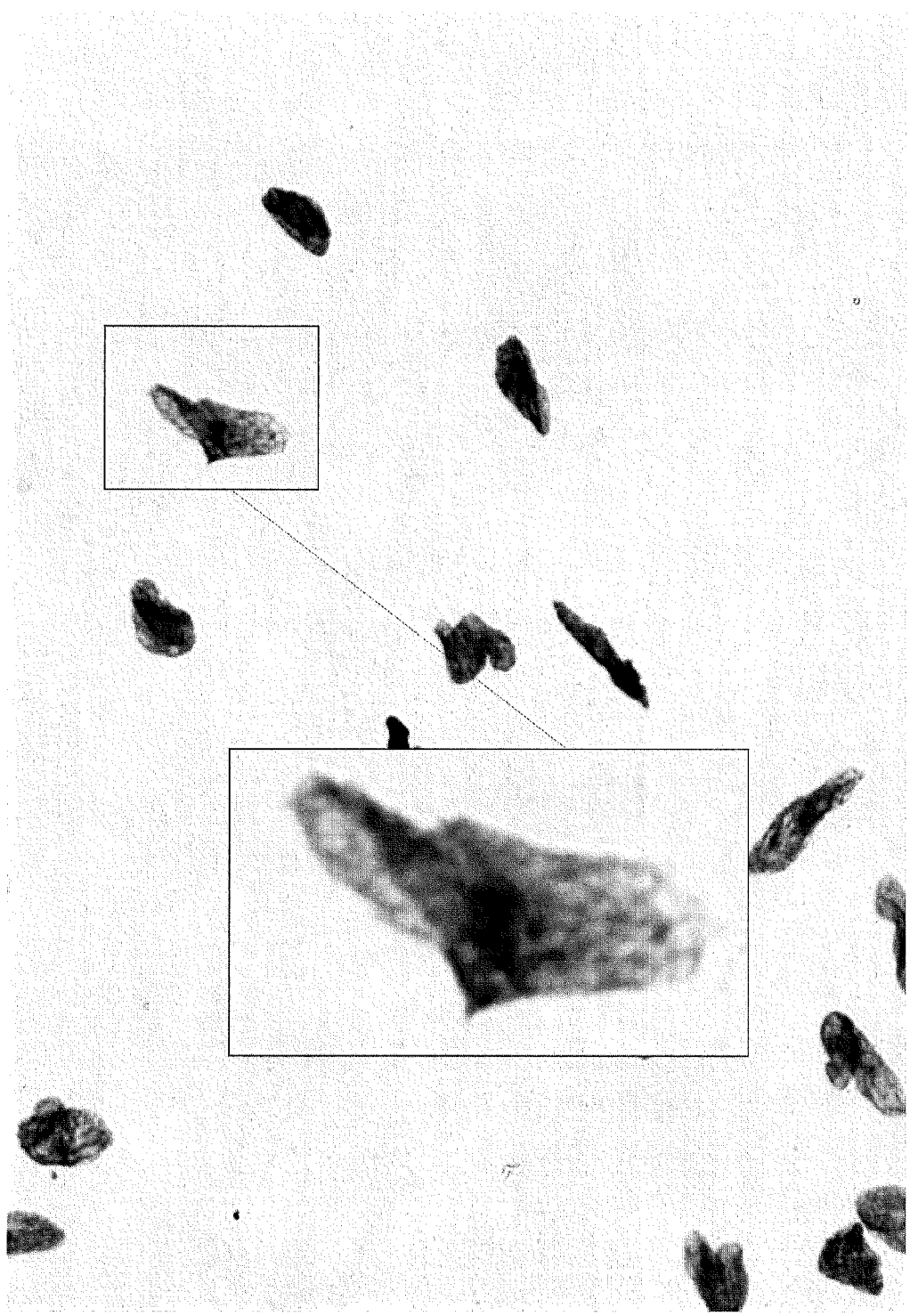
FIG. 24 shows a micrograph of metakaryotic stem cells in stenotic part of left and right pulmonary veins including another example of an irregular nucleus of a smooth muscle cell created by amitosis from a metakaryotic stem cell.
Figure 25:
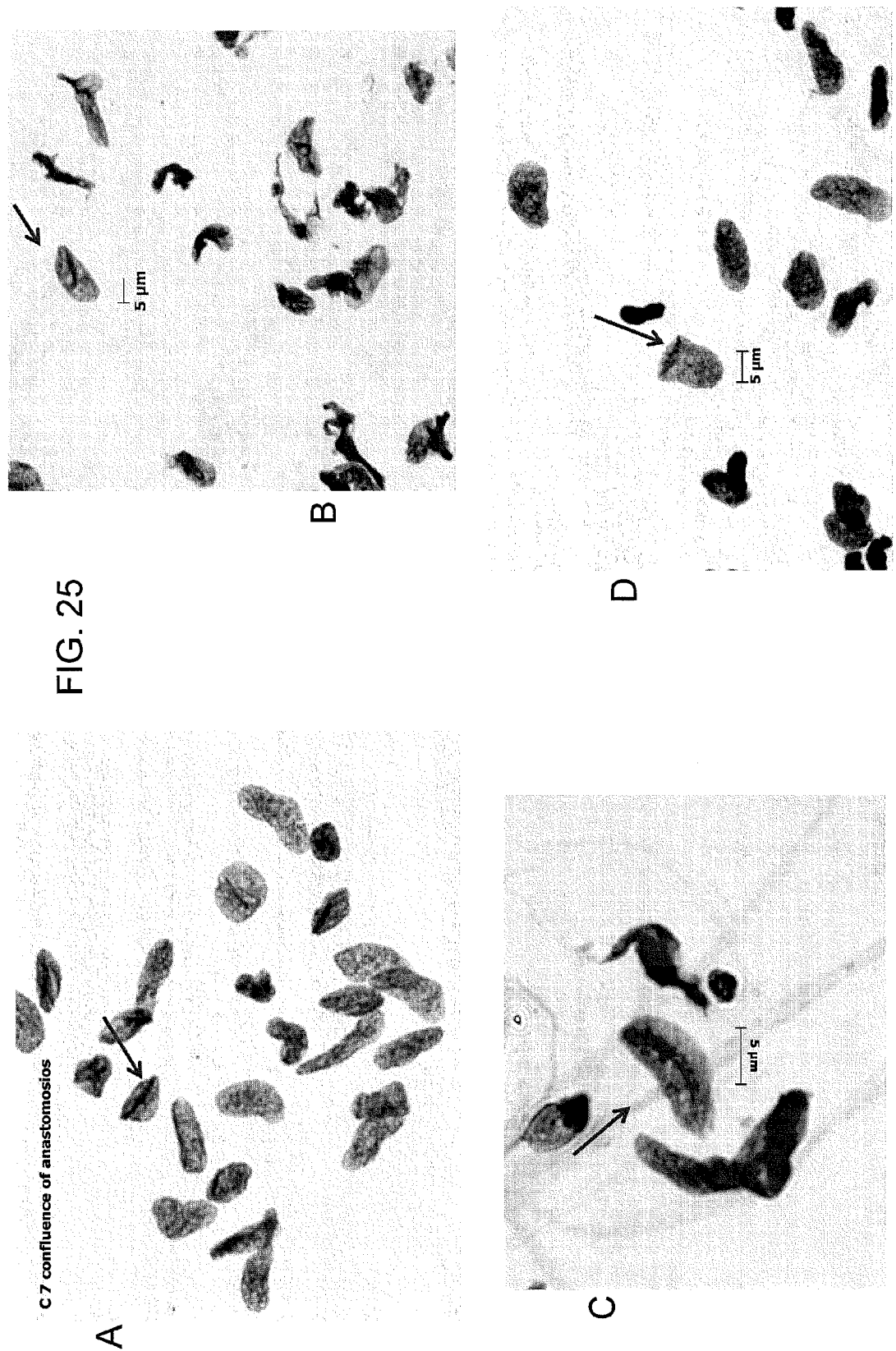
FIGS. 25A-D are micrographs of confluence of anastomosis/restenosis showing groups of smooth muscle cells and their "parent" metakaryotic stem cells.
Figure 26:
FIG. 26 shows a micrograph of non-mitotic asymmetric nuclear fission at the site of anastomosis, in particular showing irregular nuclei (purple) of smooth muscle cells arising by asymmetric amitosis from metakaryotic stem cells.
Figure 27:
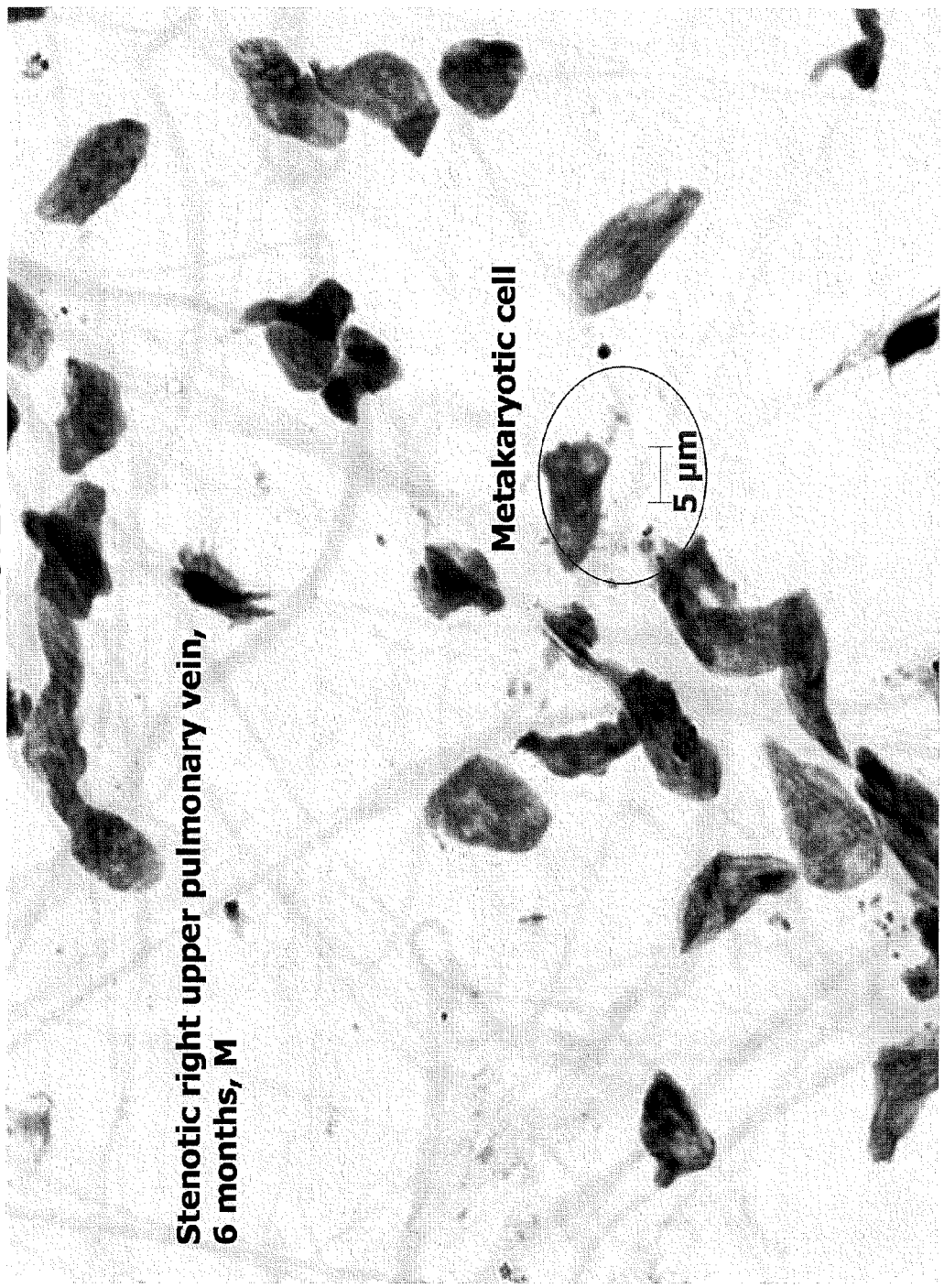
FIG. 27 is a micrograph illustrating another example of stenotic tissues; notable by absence in this and all figures are smooth muscle cells dividing by mitosis or amitosis.

Visualization of Metakaryotic Cells in a Patient with Post-Transplant Restenosis A child 2 years old who was recently transplanted, suffered rejection, and over 1 month had rapid progression of diffuse coronary atherosclerosis. The child suffered a cardiac arrest because of this rapidly progressing coronary disease. The child was stabilized on emergent cardiopulmonary bypass support for 6 days until a heart became available. The child's diseased heart was explanted and a new one was provided. FIG. 6 and FIG. 7 include micrographs of freshly-fixed tissues prepared from this subject. FIGS. 6C-D are micrographs showing major blood vessels in pig.

Example 3

Vasculogenesis and Bladder Polyp Catheter Injury

FIGS. 2-4 illustrate vasculogensis. FIG. 17B includes a micrograph of a bladder polyp injury.

Example 4

Wound Healing in the Skin of a 6 Month Old Human Child

FIGS. 18-21 are micrographs of wound healing in the skin of a 6 month old human child.

Example 5

Post-surgical "Galloping Atherosclerosis" i.e. Restenosis in Pulmonary Vein and Rejected Heart Transplant of 2 Year Old Child The micrographs in FIGS. 6-16 10-13 and 16-18 were prepared as described above.

Example 6

Additional Observations

FIG. 22 et seq. include micrographs of inter alia, stenotic veins, confluence of anastomosis, and normal adult mouse colon.

Example 7

In Vivo Screening to Identify Agents to Treat Wound Healing Disorders

Animals are maintained in approved facilities in accordance with proper ethical and experimental guidelines.

Control and experimental guinea pigs are subject to vascular insult prior to treatment. Experimental animals are administered a candidate agent at a dose of between 0.01-100 mg/kg/day. Control animals are mock-treated. After 1, 2, 3, 4, 5, 6, 7, 8, 9, or 10 days, animals are sacrificed and the region subject to vascular insult is evaluated histologically by removing the vascular tissue and associated adventitia, fixing and staining the tissues, using methods that preserve metakaryotic stem cells. The tissue sample containing the previously-injured vascular tissue is evaluated in control and experimental animals for the total number of metakaryotic stem cells, the total number of proliferating metakaryotic stem cells, and the location of the metakaryotic stem cells—e.g., relative to the intimal surface of the damaged vessel and the associated adventitia, for example, to determine the effect on migration of the metakaryotes from the adventitia to the intimal surface of the damaged blood vessel. Agents that reduce the total number of metakaryotic stem cells, the total number of proliferating metakaryotic stem cells, or the migration of metakaryotic stem cells are expected to be efficacious for the treatment of wound healing disorders, such as blood vessel wound healing disorders.

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for detecting bell-shaped nuclei in metakaryotic stem cells in a subject, the method comprising:
   a) obtaining a vascular tissue sample from the subject suspected of having neointimal hyperplasia or restenosis;
   b) partially dissociating the tissue sample by macerating and spreading the tissue sample by a method that substantially preserves the integrity of bell-shaped nuclei of metakaryotic stem cells in the tissue sample, the nuclei having maximum diameters from about 10-50 microns;
   c) fixing and staining the tissue sample to visualize the bell-shaped nuclei of the metakaryotic stem cells;
   d) detecting the presence and/or absence of metakaryotic stem cells in the subject tissue sample and in a control tissue sample.

2. The method of claim 1, wherein the restenosis is post-surgical restenosis.

3. The method of claim 1, wherein the cells are physically or chemically fixed.

4. The method of claim 3, wherein the tissue sample is frozen.

5. The method of claim 3, wherein the tissue sample is treated with one or more chemical fixing agents selected from the group consisting of: alcohols, aldehydes, organic acids and combinations thereof.

6. The method of claim 5, wherein the fixing agent comprises methanol and acetic acid.

7. The method of claim 3, wherein the cells in the tissue sample are fixed prior to cellular degradation of nuclei.

8. The method of claim 1, wherein the cells are stained, thereby allowing visualization of nuclei.

9. The method of claim 8, wherein the DNA is stained, thereby allowing visualization of the nuclei.

10. The method of claim 1, wherein the cells are fixed within 30 minutes of being isolated.

11. The method of claim 1, wherein the tissue sample is obtained from a multicellular animal.

12. The method of claim 11, wherein the multicellular animal is a vertebrate.

13. The method of claim 12, wherein the vertebrate is a mammal.

14. The method of claim 13, wherein the mammal is selected form the group consisting of: a primate, a rodent, a canine, a feline, a porcine, an ovine, a bovine, and a leporine.

15. The method of claim 14, wherein the mammal is a human.

16. The method of claim 1, wherein the tissue sample further comprises cells with heteromorphic nuclear morphotypes including: cigar-shaped nuclei, bullet-shaped nuclei, sausage-shaped nuclei, kidney-shaped nuclei, irregular spindle-shaped nuclei, and combinations thereof.

17. The method of claim 16 wherein the tissue sample comprises adventitia.

* * * * *